US012644087B2

(12) United States Patent
Allbritton et al.

(10) Patent No.: US 12,644,087 B2
(45) Date of Patent: Jun. 2, 2026

(54) METHODS TO GENERATE POLYMER SCAFFOLDS HAVING A GRADIENT OF CROSSLINKING DENSITY

(71) Applicant: The University of North Carolina at Chapel Hill, Chapel Hill, NC (US)

(72) Inventors: Nancy Allbritton, Chapel Hill, NC (US); Yuli Wang, Cary, NC (US); Hennayaka Mudiyanselage Dulan Gunasekara, Carrboro, NC (US); Christopher Sims, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 19/069,812

(22) Filed: Mar. 4, 2025

(65) Prior Publication Data

US 2025/0263647 A1      Aug. 21, 2025

Related U.S. Application Data

(63) Continuation of application No. 18/220,535, filed on Jul. 11, 2023, now abandoned, which is a continuation of application No. 16/316,139, filed as application No. PCT/US2017/043601 on Jul. 25, 2017, now abandoned.

(60) Provisional application No. 62/367,339, filed on Jul. 27, 2016.

(51) Int. Cl.
| | |
|---|---|
| *C12M 1/12* | (2006.01) |
| *C12M 1/00* | (2006.01) |
| *C12M 1/42* | (2006.01) |
| *C12N 5/00* | (2006.01) |
| *C12N 5/071* | (2010.01) |
| *G01N 33/50* | (2006.01) |

(52) U.S. Cl.
CPC ............ *C12M 25/14* (2013.01); *C12M 23/20* (2013.01); *C12M 35/08* (2013.01); *C12N 5/0062* (2013.01); *C12N 5/0679* (2013.01); *G01N 33/5014* (2013.01); *C12N 2513/00* (2013.01); *C12N 2533/54* (2013.01); *C12N 2537/10* (2013.01)

(58) Field of Classification Search
CPC ...... C12M 25/14; C12M 23/20; C12M 35/08; C12N 5/0062; C12N 5/0679; C12N 2513/00; C12N 2533/54; C12N 2537/10; G01N 33/5014; A61P 27/02
See application file for complete search history.

(56) References Cited

U.S. PATENT DOCUMENTS

| | | | |
|---|---|---|---|
| 8,946,305 B2 | 2/2015 | Liao et al. | |
| 9,040,665 B2 | 5/2015 | Wnek et al. | |
| 9,132,208 B2 | 9/2015 | Chen et al. | |
| 9,200,676 B2 | 12/2015 | Yamaguchi | |
| 9,205,172 B2 | 12/2015 | Leonard Neethling et al. | |
| 9,211,362 B2 | 12/2015 | Hwang et al. | |
| 9,272,004 B2 | 3/2016 | Nataraj et al. | |
| 9,283,301 B1 | 3/2016 | Simionescu et al. | |
| 11,193,110 B2 | 12/2021 | Allbritton et al. | |
| 2003/0017142 A1 | 1/2003 | Dimilla et al. | |
| 2005/0106717 A1 | 5/2005 | Wilson et al. | |
| 2006/0019389 A1 | 1/2006 | Yayon et al. | |
| 2006/0121609 A1 | 6/2006 | Yannas et al. | |
| 2007/0134790 A1 | 6/2007 | Gould et al. | |
| 2009/0253153 A1 | 10/2009 | Chu | |
| 2010/0047853 A1 | 2/2010 | Kuo et al. | |
| 2010/0075293 A1 | 3/2010 | Chang et al. | |
| 2012/0015003 A1 | 1/2012 | Gleeson et al. | |
| 2012/0089238 A1 | 4/2012 | Kang et al. | |
| 2014/0009378 A1 | 1/2014 | Chew | |
| 2017/0059555 A1 | 3/2017 | Iyer et al. | |
| 2017/0191026 A1 | 7/2017 | Alexander | |
| 2017/0306278 A1 | 10/2017 | Nguyen et al. | |
| 2018/0002672 A1 | 1/2018 | Allbritton et al. | |
| 2019/0211296 A1 | 7/2019 | Allbritton | |
| 2019/0382703 A1 | 12/2019 | Katayama et al. | |
| 2021/0087515 A1 | 3/2021 | Allbritton et al. | |
| 2021/0395661 A1 | 12/2021 | Allbritton et al. | |

FOREIGN PATENT DOCUMENTS

| | | |
|---|---|---|
| EP | 3250678 A1 | 12/2017 |
| EP | 3794349 A1 | 3/2021 |
| EP | 3802848 A1 | 4/2021 |
| EP | 3880785 A1 | 9/2021 |
| JP | 2009250977 A | 10/2009 |
| JP | 2011523355 A | 8/2011 |
| JP | 2012500371 A | 1/2012 |

(Continued)

OTHER PUBLICATIONS

Orban et al., "Crosslinking of collagen gels by transglutaminase," Journal of Biomedical Materials Research Part A, vol. 68A: 756-762 (2004).

Paguirigana et al., "Protocol for the fabrication of enzymatically crosslinked gelatin microchannels for microfluidic cell culture," Nat Protoc., vol. 2: 1782-1788 (2007).

Pai et al., "Photoresist with Low Fluorescence for Bioanalytical Applications," Analytical Chemistry, vol. 79: 8774-8780 (2007).

Paine et al. "Cytochrome P-450 1A1 Expression in Human Small Bowel: Interindividual Variation and Inhibition by Ketoconazole," Drug Metabolism and Disposition, vol. 27, No. 3: 360-364 (1999).

(Continued)

*Primary Examiner* — Satyendra K Singh

(74) *Attorney, Agent, or Firm* — KDW FIRM PLLC

(57) ABSTRACT

The present invention is directed to a method of making a live cell construct or a support, comprising: (a) providing a non-cellular organic polymer support having a top surface, a bottom surface, and an intermediate portion there between, and (b) contacting a cross-linking agent to one surface of said support for a time sufficient to generate a gradient of cross-linking of said polymer in said intermediate portion. Also provided are live cell constructs, supports, and methods of use of the supports and live cell constructs.

12 Claims, 5 Drawing Sheets

(56)                    References Cited

FOREIGN PATENT DOCUMENTS

| JP | 2019518443 A | 7/2019 |
|----|--------------|--------|
| JP | 6920203 B2 | 7/2021 |
| WO | 2005072419 A2 | 8/2005 |
| WO | 2005104755 A2 | 11/2005 |
| WO | 2006034365 A2 | 3/2006 |
| WO | 2009132196 A2 | 10/2009 |
| WO | 2011057219 A2 | 5/2011 |
| WO | 2012136701 A1 | 10/2012 |
| WO | 2014021778 A1 | 2/2014 |
| WO | 2014186430 A1 | 11/2014 |
| WO | 2015020614 A1 | 2/2015 |
| WO | 2016123474 A1 | 8/2016 |
| WO | 2017131839 A2 | 8/2017 |
| WO | 2018022548 A1 | 2/2018 |
| WO | 2018052953 A1 | 3/2018 |
| WO | 2018175861 A1 | 9/2018 |
| WO | 2018185321 A1 | 10/2018 |
| WO | 2018225835 A1 | 12/2018 |
| WO | 2019141824 A1 | 7/2019 |
| WO | 2019227012 A1 | 11/2019 |
| WO | 2020102682 A1 | 5/2020 |

OTHER PUBLICATIONS

Park et al., "Alterations of proliferative and differentiation potentials of human embryonic stem cells during long-term culture," Exp Mol Med., vol. 40(1): 98-108 (2008).

Parlesak et al., "Modulation of Cytokine Release by Differentiated CACO-2 Cells in a Compartmentalized Coculture Model with Mononuclear Leucocytes and Nonpathogenic Bacteria." Scandinavian Journal of Immunology vol. 60: 477-485, (2004).

Pedron S. et al., "Microfluidic approaches for the fabrication of gradient crosslinked networks based on poly(ethylene glycol) and hyperbranched polymers for manipulation of cell interactions," J Biomed Mat Res., vol. 96(1): 196-203 (2011).

Peery et al., "Burden of gastrointestinal diseases in the United States: 2012 Update," Gastroenterology, vol. 143, e1173: 1179-1187 (2012).

Pelaseyed et al., "The mucus and mucins of the goblet cells and enterocytes provide the first defense line of the gastrointestinal tract and interact with the immune system," Immunological reviews, vol. 260: 8-20 (2014).

Petersen et al., "Generation of L Cells in Mouse and Human Small Intestine Organoids," Diabetes, vol. 63(2): 410-420 (2014).

Peyton et al., "Marrow-Derived Stem Cell Motility in 3D Synthetic Scaffold Is Governed by Geometry Along With Adhesivity and Stiffness," Biotechnology and Bioengineering, vol. 108: 1181-1193 (2011).

Provenzano et al., "Mechanical signaling through the cytoskeleton regulates cell proliferation by coordinated focal adhesion and Rho GTPase signaling," J. Cell Sci, vol. 124: 1195-1205 (2011).

Puzan et al., "Enteric Nervous System Regulation of Intestinal Stem Cell Differentiation and Epithelial Monolayer Function." Scientific Reports, vol. 8: 6313 (2018).

Qu et al., "Maturation State and Matrix Microstructure Regulate Interstitial Cell Migration in Dense Connective Tissues," Scientific Reports, vol. 8: 3295 (2018).

Quaroni et al., "Epithelioid Cell Cultures from Rat Small Intestine," J. Cell Biology, vol. 80: 248-265 (1979).

Quaronia, "Short-term primary culture of epithelial cells from human colon," Gastroenterology, vol. 96: 535-536 (1989).

Quigley, "Gut bacteria in health and disease." Gastroenterology & hepatology, vol. 9: 560-569 (2013).

Ramadan et al., "NutriChip: nutrition analysis meets microfliudics," Lab Chip, vol. 13: 196-203 (2013).

Ramanujan et al., "Diffusion and Convection in Collagen Gels: Implications for Transport in the Tumor Interstitium," Biophysical Journal, vol. 83: 1650-1660 (2002).

Raredon et al., "A Rotating Bioreactor for Scalable Culture and Differentiation of Respiratory Epithelium." Cell Medicine vol. 7: 109-121 (2012).

Ren et al., "Short-Chain Fatty Acids Induce Intestinal Epithelial Heat Shock Protein 25 Expression in Rats and IEC 18 Cells," Gastroenterology, vol. 121: 631-639 (2001).

Rexius-Hall et al., "Microfluidic platform generates oxygen landscapes for localized hypoxic activation," Lab on a Chip, vol. 14: 4688-4695 (2014).

Rodriguez-Serrano et al., "Differentiation of intestinal Epithelial Cells Mediated by Cell Confluence and/or Exogenous Nucleoside Supplmentation," Cell Tissues Organs, vol. 191: 478-488 (2010).

Roeder et al. "Compliance, elastic modulus, and burst pressure of small-intestine submucosa (SIS), small-diameter vascular grafts," J Biomed Mater Res., vol. 47: 65-70 (1999).

Rogier et al., "Secretory IgA is Concentrated in the Outer Layer of Colonic Mucus along with Gut Bacteria," Pathogens, vol. 3: 390-403 (2014).

Rosa ACP et al., "Interaction of *Escherichia coli* strains of non-EPEC serogroups that carry eae and lack the EAF and stx gene sequences with undifferentiated and differentiated intestinal human Caco-2 cells," FEMS Microbiology Letters, vol. 200: 117-122 (2001).

Rother et al., "Cytoskeleton remodelling of confluent epithelial cells cultured on porous substrates," Journal of the Royal Society Interface, vol. 12: 20141057 (2015).

Ruemmele et al., "Butyrate induced Caco-2 cell apoptosis is mediated via the mitochondrial pathway," Gut, vol. 52: 94-100 (2003).

Sampson et al., "Gut microbiota regulate motor deficits and neuroinflammation in a model of Parkinson's disease," Cell, vol. 167, e1412: 1469-1480 (2016).

Sato et al., "Long-term Expansion of Epithelial Organoids From Human Colon, Adenoma, Adenocarcinoma, and Barrett's Epithelium." Gastroenterology vol. 141: 1762-1772 (2011).

Sato et al., "Single Lgr5 stem cells build crypt-villus structures in vitro without amesenchymal niche," Nature, vol. 459: 262-U147 (2009).

Sato et al., "Photoactivation of a nanoporous crystal for on-demand guest trapping and conversion," Nature Materials, vol. 9 (Aug. 2010).

Sato et al., "Paneth Cells constitute the niche for Lgr5 stem cells in intestinal crypts," Nature, vol. 469(7330): 415-418 (2011).

Schindelin et al., "Fiji—an Open Source platform for biological image analysis," Nature Methods, vol. 9: 676 (2012).

Schneeberger et al., "Intestinal epithelial cell polarity defects in disease: Lessons from microvillus inclusion disease," Disease Models & Mechanisms, vol. 11 (2018).

Schuijers et al., "Adult mammalian stem cells: The role of Writ, Lgr5 and R-spondins," The EMBO Journal, vol. 31: 2685-2696 (2012).

Schwartz et al., "Vasoactive intestinal peptide stimulation of adenylate cyclase and active electrolyte secretion in intestinal mucosa." Journal of Clinical Investigation, vol. 54: 536-544 (1974).

Seidelin et al., "Simple and efficient method for isolation and cultivation of endoscopically obtained human colonocytes," Am. J. Physiol.- Gastroint. Liver Physiol., vol. 285: G1122-G1128 (2003).

Semrau et al., "Studying lineage decision-making in vitro; emerging concepts and novel tools," Annual review of cell and developmental biology, vol. 31: 317-345 (2016).

Seo et al., "Epithelial monolayer culture system for real-time single-cell analyses," Phys Rep., vol. 2(4): e12002: 1-3 (2014).

Seyedhassantehrani et al., "Dynamic behaviours of astrocytes in chemically modified fibrin and collagen hydrogels," Integrative Biology (2016).

Shah et al. "Role of Caco-2 cell monolayers in prediction of intestinal drug absorption," Biotechnol. Prog., vol. 22: 186-198 (2006).

Shah et al., "A microfluidics-based in vitro model of the gastrointestinal human-microbe interface," Nature Communications, vol. 7 (2018).

Shields et al., "Absorption and secretion of water and electrolytes by the intact colon in a patient with primary aldosteronism." British Medical Journal vol. 1: 93-96 (1968).

(56) References Cited

OTHER PUBLICATIONS

Shimamura et al., "Relationship Between Oxygen Sensitivity and Oxygen Metabolism of *Bifidobacterium* Species," Journal of Dairy Science, vol. 75: 3296-3306 (1992).

Shreiner et al., "The gut microbiome in health and in disease," Current opinion in gastroenterology, vol. 31: 69 (2015).

Simon et al., "Polymer-Based Mesh as Supports for Multi-layered 3D Cell Culture and Assays," Biomaterials., vol. 35 (1): 1-21 (2014) abstract.

Simon et al., "The Role of Oxygen Availability in Embryonic Development and Stem Cell Function," Nature Reviews: Molecular Cell Biology, vol. 9, 285 (2009).

Skilimowski et al., "Microfludic dissolved oxygen gradient generator biochip as a useful tool in bacterial biofilm studies," Lab on a chip, vol. 10: 2162-2169 (2010).

Sommer et al., "The resilience of the intestinal microbiota influences health and disease," Nat Rev Microbiol, vol. 15: 630-638 (2017).

Kaiko et al., "The colonic crypt protects stem cells from microbiota-derived metabolites," Cell, vol. 165: 1708-1720 (2016).

Kaminsky et al., "Small Intestinal Cytochromes P450," Critical Reviews in Toxicology, vol. 21: 407-422 (1992).

Karve et al., "Intestinal organoids model human responses to infection by commensal and Shiga toxin producing *Escherichia coli*," PloS one, vol. 12: e0178966 (2017).

Kelly et al., "Fundamental role for HIF-1α in constitutive express of human β defensin-1," Mucosal Immunology, vol. 6, No. 6: 1110-1118 (Nov. 2013).

Kharkar et al. (2013), "Designing degradable hydrogels for orthogonal control of cell microenvironments," Chem. Soc. Rev., vol. 42: 7335-7372 (2013).

Kim et al., "Contributions of microbiome and mechanical deformation to intestinal bacterial overgrowth and inflammation in a human gut-on-a-chip," Proceedings of the National Academy of Sciences, vol. 113: E7-E15 (2016).

Kim et al., "Human gut-on-a-chip inhabited by microbial flora that experiences intestinal peristalsis-like motions and flow," Lab Chip, vol. 12: 2165-2174 (2012).

Kim et al., "Neonatal acquisition of *Clostridia* species protects against colonization by bacterial pathogens," Science, vol. 356: 315-319 (2017).

Koch et al., "Plasma vasoactive intestinal polypeptide concentration determination in patients with diarrhea," Gastroenterology, vol. 100: 99-106 (1991).

Koh et al., "Passing the baton: the HIF switch," Trends in Biochemical Sciences, vol. 37: 364-372 (2012).

Koh et al., "From Dietary Fiber to Host Physiology: Short-Chain Fatty Acids as Key Bacterial Metabolites," Cell, vol. 165: 1332-1345 (2016).

Kosinski et al., "Gene expression patterns of human colon tops and basal crypts and BMP antagonists as intestinal stem cell niche factors," Proc. Natl. Acad. Sci. U S. A., vol. 104: 15418-15423 (2007).

Kozuka et al., "Development and Characterization of a Human and Mouse Intestinal Epithelial Cell Monolayer Platform," Stem cell reports, vol. 9: 1976-1990 (2017).

Lamberti et al., "PDMS membranes with tunable gas permeability for microfluic applications," Research Advances, vol. 4: 61415-61419 (2014).

Lancaster et al., "Organogenesis in a dish: Modeling development and disease using organoid technologies," Science, vol. 345(6194): 283 (2014).

Leblanc et al., "Bacteria as viatmin suppliers to their host: a gut microbiota perspective," Current Opinion in Biotechnology, vol. 24: 160-168 (2013).

Leffler et al., "Clostridium difficile infection," New England Journal of Medicine, vol. 372: 1539-1548 (2015).

Lehr et al., "An estimate of turnover time of intestinal mucus gel layer in the rat in situ loop," International Journal of Pharmaceutics, vol. 70: 235-240 (1991).

Leonel et al., "Butyrate: Implications for intestinal function," Current Opinion in Clinical nutrition & Metabolic Care, vol. 15: 474-479 (2012).

Lesuffleur et al., "Growth adaptation to methotrexate of HT-29 human colon carcinoma cells is associated with their ability to differentiate into columnar absorptive and mucus-secreting cells," Cancer Research vol. 50, : 6334-6343 (1990).

Levenberg et al., "Differentiation of human embryonic stem cells on three-dimensional polymer scaffolds," PNAS, vol. 100(22): 12741-12746 (2003).

Li et al., "Role of mechanical factors in fate decisions of stem cells," Regenerative medicine, vol. 6: 229-240 (2011).

Lin et al., "Air-liquid interface (SLI) culture of human bronchial epithelial cell monolayers as an in vitro model for airway drug transport studies," Journal of Pharmaceutical Sciences, vol. 96: 341-350 (2007).

Liu et al., "Chemistry of Periodate-Mediated Cross-Linking of 3.4-Dihydroxylphenylalanine (DOPA)-Containing Molecules to Proteins," J Am Chem Soc., vol. 29: 15228-15235 (2006).

Liu et al., "A Simple, Cross-linked Collagen Tissue Substitute for Corneal Implantation," Invest. Ophthalmol Invest. Ophthalmol. Vis. Sci., vol. 47: 1869-1875 (2006).

Lü et al., "Differential regulation of morphology and stemness of mouse embryonic stem cells by substrate stiffness and topography," Biomaterials, vol. 35: 3945-3955 (2014).

Lüdeking et al., "Osmotic changes and ethanol modifyTFF gene expression in gastrointestinal cell lines." Febs Letters vol. 439: 180-184 (1998).

Lynch et al., "The Human Intestinal Microbiome in Health and Disease," The New England Journal of Medicine, vol. 375: 2369-2379 (2016).

Maenosono et al. "A Transparent Polyimide Film as a Biological Cell Culture Sheet with Microstructures," Journal of Biomaterials and Nanobiotechnology, vol. 5: 17-23.(2014).

Mahida et al., "Effect of Clostridium difficile toxin A on human intestinal epithelial cells: induction of interleukin 8 production and apoptosis after cell detachment." Gut, vol. 38: 337-347 (1996).

Maina, "Structure, function and evolution of the gas exchangers: comparative perspectives," J Anat., vol. 201: 281-304 (2002).

Markov et al., "Variation in diffusion of gases through PDMS due to plasma surface treatment and storage conditions," Biomedical Microdevices, vol. 16: 91-96 (2014).

Martignoni et al., Abstract of "An in vivo and in vitro comparison of CYP induction in rat liver and intestine using slices and quantitative RT-PCR," Chemico-Biological Interactions, vol. 151, Iss. 1: 1-11 (2004).

Martignoni, "Species and strain differences in drug metabolism in liver and intestine," University of Groningen/UMCG: 1-136 (2006).

Marzorati et al., "The HMI™ module: A new tool to study the Host-Microbiota interaction in the human gastrointestinal tract in vitro," BMC Microbiology, vol. 14, Article No. 133 (2014).

Matsuzawa et al., "Construction of three-dimensiona liver tissue models by cell accumulation technique and maintaining their metabolic functions for long-term culture without medium change," J Biomed Mater Res Part A., vol. 103(4): 1554-1564 (Apr. 2015).

Mills et al., "Gastric epithelial stem cells," Gastroenterology, vol. 140 (2): 414-424 (Feb. 2011).

Moon et al., "Development of a primary mouse intestinal epithelial cell monolayer culture system to evaluate factors that modulate IgA transcytosis," Mucosal Immunol., vol. 7: 818-828 (2014).

Munoz-Pinto et al, "Lamina Propria Cellularity and Collagen Composiiton : An Integrated Assesment of Structure in Humans," Annals of Otology, Rhinology, and Laryngology (2009).

Murgia et al., "The role of mucus on drug transport and its potential to affect therapeutic outcomes," Adv Drug Deliv Rev, vol. 124: 82-97 (2018).

Nagpal et al., "Gut microbiota: The next-gen frontier in preventative and therapeutic medicine?," Frontiers in Medicine, vol. 1(2014).

Navabi et al., "Gastrointestinal Cell Lines Form Polarized Epithelia with an Adherent Mucus Layerx when Cultured in Semi-Wet Interfaces with Mechanical Stimulation." Plos One vol. 8: e68761 (2013).

(56) References Cited

OTHER PUBLICATIONS

Noel et al., "A primary human macrophage-enteroid co-culture model to investigate mucosal gut physiology and host pathogen interactions." Scientific Reports, vol. 7: 45270 (2017).

Nusrat et al., "Clostridium difficile Toxins Disrupt Epithelial Barrier Function by Altering Membrane Microdomain Localization of Tight Junction Proteins." Infection and Immunity, vol. 69: 1329-1336 (2001).

O'Boyle et al., "Temporal dynamics of ovine airway epithelial cell differentiation at an air liquid interface." Plos One vol. 12: e0181583 (2017).

Ootani et al., "An air-liquid interface promotes the differentiation of gastric surface mucous cells (GSM06) in culture." Biochemical and Biophysical Research Communications vol. 271: 741-746 (2000).

Ootani et al., "Sustained in vitro intestinal epithelial culture within a Wnt-dependent stem cell niche." Nature Medicine vol. 15: 1-U140 (2009).

Oppegard et al., "A microfabricated platform for establishing oxygen gradients in 3-D construcs," Biomedical Midrodevices, vol. 15: 407-414 (2013).

Oppegard et al., "Modulating temporal and spatial oxgenation over adherent cellular cultures," PLoS One, vol. 4, e6891 (2009).

Oppegard et al., "Precise control over the oxygen conditions within the Boyden chamber using a microfabricated insert," Lab on a Chip, vol. 10: 2366-2373 (2010).

Song et al., "Collagen scaffolds derived from a marine source and their biocompatibility," Biomaterials, vol. 27: 2951-2961 (2006).

Soofi et al., "The elastic modulus of Matrigel™ as determined by atomic force microscopy" Journal of Structural Biology, vol. 167: 216-219 (2009).

Speer et al., "Molecular transport through primary human small intestinal monolayers by culture on a collagen scaffold with a gradient of chemical cross-linking," Journal of Biological Engineering (Apr. 27, 2019).

Spence et al., "Directed differentiation of human pluripotent stem cells into intestinal tissue in vitro," Nature, vol. 470 (7332): 105-109 (2011).

Stelzner et al., Consortiu,Am. J Physiol.-Gastroint. Liver Physiol., 2012, 302, G1359-G1363.

Sternini et al., "Enteroendocrine cells: a site of 'taste'in gastrointestinal chemosensing," Current Opinion in Endocrinology, Diabetes, and Obesity, vol. 15: 73 (2008).

Strater et al., "Rapid Onset of Apoptosis In Vitro Follows Disruption of beta1-Integrin/Matrix interactions in Human Colonic Crypt Cells," Gastroenterology (1996).

Sundararaghavan et al., "Genipin-induced changes in collagen gels: Correlation of mechanical properties to fluorescence," Journal of Biomedical Materials Research Part A, vol. 87A: 308-320 (2008).

Sung et al., "Microfabricated mammalian organ systems and their integration into models of whole animals and humans," Lab Chip, vol. 13(7): 1201-1212 (2013).

Sung et al., "Microscale 3-D hydrogel scaffold for biomimetic gastrointestinal (GI) tract model," Lab Chip, vol. 11: 389-392 (2011).

Szpak, "Fish bone chemistry and ultrastructure: implications for taphonomy and stable isotope analysis," J. Archaeol. Sci., vol. 38: 3358-3372 (2011).

Szymanski et al., "Adaptation of High-Throughput Screening in Drug Discovery—Toxicological Screening Tests," Int J Mol Sci., vol. 13: 427-452 (2012) abstract.

Takano et al., In Engineering in Medicine and Biology Society (EMBC), 2013 35th Annual International Conference of the IEEE: 4474-4477 (IEEE).

Tang et al., "Utilization of a Human Intestinal Epithelial Cell Culture System (Caco-2) for Evaluating Cytoprotective Agents," Pharm Res, vol. 10(11): 1620-1626 (1993).

Terryn et al., "Recent advances in lineage differentiation from stem cells: hurdles and opportunities?," F1000Resarch, vol. 7 (2018).

Tong et al., "Towards a defined ECM and small molecule based monolayer culture system for the expansion of mouse and human intestinal stem cells," Biomaterials, vol. 154: 60-73 (2018).

Transwell® permeable supports, 8 pages (2007).

Tremlett et al., "The gut microbiome in human neurological disease: a review," Annals of Neurology (2017).

Tsubouchi, "Kinetic analysis of epithelial cell migration in the mouse descending colon." Developmental Dynamics, vol. 161: 239-246 (1981).

Tsujii et al., "Colonic mucosal hemodynamics and tissue oxygenation in patients with ulcerative colitis: Investigation by organ reflectance spectrophotometry," Journal of Gastroenterology, vol. 30: 183-188 (1995).

Tu et al., "Effect of osmotic response element binding protein on mucus secretion with hypertonicity in human airway epithelial cells," Zhonghus Yi Xue Za Zhi, vol. 91: 549-553 (2011) [ English Abstract].

Uchida et al., "Generation of an oxygen gradient in a microfluidic device and cellular analysis in hypoxia," Advanced Biomedical Engineering, vol. 2: 143-149 (2013).

Ulluwishewa et al., "Live Faecalibacterium prausnitzii in an apical anaeobic model of the intestinal epithelial barrier," Cellular Microbiology, vol. 17: 226-240 (2015).

Umar, "Intestinal Stem Cells," Curr. Gastroenterol Rep., vol. 12(5): 340-348 (Oct. 2010).

Varia et al., "Pimonidazole: a novel hypoxia marker for complementary study of tumor hypoxia and cell proliferation in cervical carcinoma," Gynecologic Oncology, vol. 71: 270-277 (1998).

Valenta et al., "The many faces and functions of β-catenin," The EMBO Journal, vol. 31: 2714-2736 (2012).

Vallo et al., "Elastic Modulus and Yield Stress of EpoxyNetworks in the Glassy State," Polymer Gels and Networks, vol. 1: 257-266 (1993).

Van Es et al., "Dll1+ secretory progenitor cells revert to stem cells upon crypt damage," Nature cell biology vol. 14, 1099 (2012).

Vandussen et al. "Development of an enhanced human gastrointestinal epithelial culture system to facilitate patient-based assays," Gut, vol. 64: 911-920 (2015).

Voth et al., "Clostridium difficile toxins: mechanism of action and role in disease." Clinical microbiology reviews, vol. 18: 247-263 (2005).

Vrana et al. "EDC/NHS cross-linked collagen foams as scaffolds for artificial corneal stroma," Journal of Biomaterials Science—Polymer Edition, vol. 18, No. 12: 1527-1545 (2007).

Wagner et al., "The rate of oxygen utilization by cells," Free Radical Biology & Medicine, vol. 51: 700-712 (2011).

Waligora et al., "Clostridium difficile cell attachment is modified by environmental factors," Applied and Environmental Microbiology, vol. 65: 4234-4238 (1999).

Walsh et al., "Emulation of Colonic Oxygen Gradients in a Microdevice," SLAS Technology: Translating Life Sciences Innovation (2017).

Wang et al., "Bioengineered Systems and Designer Matrices that Recapitulate the Intestinal Stem Cell Niche," Cell Mol Gastroenterol Hepatol, vol. 5, e441: 440-453 (2018).

Wang et al., "Capture and 3D culture of colonic crypts and colonoids in a microarray platform," Lab Chip, The Royal Society of Chemistry, vol. 13: 4625-4634 (2013).

Wang et al., "In vitro generation of colonic epithelium from primary cells guided by microstructures," Lab Chip, vol. 14: 1622-1631 (2014).

Wang et al., "Influence of micro-well biomimetic topography on intestinal epithelial Caco-2 cell phenotype," Biomaterials, vol. 30: 6825-6834 (2009).

Wang et al., "Isolation and Characterization of Intestinal Stem Cells Based on Surface Marker Combinations and Colony-Formation Assay," Gastroenterology, vol. 145(2): 383-395 (2013).

Wang et al., "A microengineered collagen scaffold for generating a polarized crypt-architecture of human small intestinal epithelium," Biomaterials, vol. 128: 44-45 (2017).

Wang et al., "Analysis of Interleukin 8 Secretion by a Stem-Cell-Derived Human-Intestinal-Epithelial-Monolayer Platform." Analytical Chemistry vol. 90: 11523-11530 (2018).

(56)          References Cited

OTHER PUBLICATIONS

Wang et al., "Building a Thick Mucus Hydrogel Layer to Improve the Physiological Relevance of In Vitro Primary Colonic Epithelial Models," Cellular and Molecular Gastroenterology and Hepatology, vol. 8, Iss. 4: 653-655 (Jul. 2019).

Wang et al., "Formation of Human Colonic Crypt Array by Application of Chemical Gradients Across a Shaped Epithelial Monolayer", Cellular and Molecular Gastroenterology and Hepatology. vol. 5, No. 2: 113-130 (2018).

Wang et al., "In vitro Generation of Mouse Colon Crypts." ACS biomaterials science & engineering, vol. 3: 2502-2513 (2017).

Wang et al., "Self-renewing monolayer of primary colonic or rectal epithelial cells," Cellular and Molecular Gastroenterology and Hepatology (2017).

Wang et al., "Synergic effects of crypt-like topography and ECM proteins on intestinal cell behavior in collagen based membranes," Biomaterials, vol. 31, Iss. 29: 7586-7598 (2010).

Wapnir et al., "Regulation mechanisms of intestinal secretion: implications in nutrient absorption." The Journal of Nutritional Biochemistry vol. 13: 190-199 (2002).

Ward et al., "Oxygen in the regulation of intestinal epithelial transport," The Journal of Physiology, vol. 592: 2473-2489 (2014).

Watson "An in vivo model of human small intestine using pluripotent stem cells," Nature Medicine, vol. 20(11): 1310-1314 (2014).

Wei et al., "Fatty Acid Synthase Modulates Intestinal Barrier Function through Palmitoylation of Mucin 2," Cell Host & Microbe, vol. 11: 140-152 (2012).

Hokari et al., "Vasoactive intestinal peptide upregulates MUC2 intestinal mucin via CREB/ATF1," American Journal of Physiology—Gastrointestinal and Liver Physiology, vol. 289, No. 5: G949-G959 (2005).

Canadian Office Action in CA Application No. 3093585, dated Apr. 25, 2025, 6 pages.

Ahmad et al., "Optimizing Wnt-3a and R spondin1 concentrations for stem cell renewal and differentiation in intestinal organoids using a gradient-forming microdevice," RSC Advances, vol. 5: 74881-74891 (2015).

Ahmad et al., "Optimizing Wnt-3a and R-spondin1 concentrations for stem cells: critical drivers of epithelial homeostasis and regeneration," Nature reviews molecular cell biology, vol. 15: 19 (2014).

Alipour et al., "Measurement of Vocal Folds Elastic Properties for Continuum Modeling," Journal of Voice, vol. 26 (6): 816.e21-816.e29 (2012).

Allen et al., "Adherent and soluble Mucus in the Stomach and Duodenum," Digestive Diseases and Sciences, vol. 30: 55S-62S (1985).

Anonye et al., "Probing Clostridium difficule infection in innovative human gut cellular models," BioRXiv, vol. 269035: 28 pages (2018).

Anonye et al., "Probing host-anaerobe interactions in innovative human gut cellular models," BioRxiv, 43 pages (2018) <doi: 10.1101/269035 >.

Autrup et al., "Explant culture of human colon," Gastroenterology, vol. 74: 1248-1257 (1978).

Barker et al., "The intestinal stem cell," Genes & Development, vol. 22: 1856-1864 (2008).

Barker, "Adult intestinal stem cells: critical drivers of epithelial homeostasis and regeneration," Nature Reviews Molecular Cell Biology, vol. 15: 19-33 (2014).

Barkla et al., "The fate of epithelial cells in the human large intestine," Pathology, vol. 31: 230-238 (1999).

Bartfeld, "Modeling infectious diseases and host-microbe interactions in gastrointestinal organoids," Developmental biology, vol. 420: 262-270 (2016).

Bartsch et al., "Establishment of a Long-Term Culture System for Rat Colon Epithelial Cells," In Vitro Cell. Dev. Biol.—Animal, vol. 40: 278-284 (2004).

Basak et al., "Induced quiescence of Lgr5+ stem cells in intestinal organoids enables differentiation of hormone-producing enteroendocrine cells," Cell Stem Cell, vol. 20: 177-190 e4 (2017).

Belchior et al., "Stem cells and biopharmaceuticals: Vital in the growth of tissue-engineered small intestine," Seminars in. Pediatric Surgery, vol. 23(3): 141-149 (2014).

Bernstam et al., "Keratinocytes grown at the air liquid interface." In Vitro Cellular Developmental Biology, vol. 22: 695-705 (1986).

Bertout et al., "The impact of O2 availability on human cancer," Nature Reviews Cancer B, vol. 967: 22 pages (2008).

Bhat et al., "The limiting role of mucus in drug absorption: drug permeation through mucus solution," International Journal of Pharmaceutics, vol. 126, No. 1-2: 179-187 (Dec. 1995).

Birchenough et al., "A sentinel goblet cell guards the colonic crypt by triggering Nlrp6-dependent Muc2 secretion," Science, vol. 352: 1535-1542 (2016).

Bishop et al., "Regulation of Caco-2 cell proliferation by basolateral membrane epidermal growth factor receptors," Am J. Physiol, vol. 267, No. 5(1): 892-900 (1994).

Blouin et al., "Butyrate elicits a metabolic switch in human colon cancer cells by targeting the pyruvate dehydrogenase complex," International Journal of Cancer, vol. 128: 2591-2601 (2011).

Boccellato et al., "Polarised epithelial monolayers of the gastric mucosa reveal insights into mucosal homeostasis and defence against infection," Gut, vol. 68: 400-413 (2019).

Booth et al., "The isolation and culture of adult mouse colonic epithelium," Epithelial Cell Biol., vol. 4: 76-86 (1995).

Brennan et al., "A 3D-printed oxygen control insert for a 24-well plate," PLoS One, vol. 10, e0137631: 9 pages (2015).

Brittan et al., "Stem Cell in Gastrointestinal Structure and Neoplastic Development," Gut, vol. 53: 899-910 (2004).

Buchwald, "FEM-based oxygen consumption and cell viability models for avascular pancreatic islets," Theoretical Biology and Medical Modeling, vol. 6, No. 5: 13 pages (2009).

Byrne et al., "Methods to study the tumor microenvironment under controlled oxygen conditions," Trends in Biotechnology, vol. 32: 556-563 (2014).

Cani, "Gut microbiota—At the intersection of everything?," Nature Reviews Gastroenterology & Hepatology, vol. 14: 321-322 (2017).

Carlson et al., "Engineering the Mucus Barrier," Annual Review of Biomedical Engineering, vol. 20: 197-220 (2018).

Cayo et al., "Sodium butyrate activates Notch1 signaling, reduces tumor markers, and induces cell cycle arrest and apoptosis in pheochromocytoma", American Journal of Translational Research, vol. 1: 178-183 (2009).

Cell Culture Inserts, 0.4um Falcon MG. Scientific 2014.

Chen et al., "Generation of oxygen gradients in microfluic devices for cell culture using spatially confined chemical reactions," Lab on a Chip, vol. 11: 3626-3633 (2011).

Chen et al., "Robust bioengineered 3D functional human intestinal epithelium," Scientific Reports, vol. 5, No. 13708: 11 pages (2015).

Chowdhury et al., "Soft Substrates Promote Homogeneous Self-Renewal of Embryonic Stem Cells via Downregulating Cell-Matrix Tractions," PloS one, vol. 5: e15655 (2010).

Colgan et al., "Epithelial exposure to hypoxia modulates neutrophil transepithelial migration," Journal of Experimental Medicine, vol. 184: 1003-1015 (1996).

Colgan et al., "Hypoxia: an alarm signal during intestinal inflammation," Nature Reviews Gastroenterology & Hepatology, vol. 7: 281-287 (2010).

Costello et al., "Synthetic Small Intestinal Scaffolds for Improved Studies of Intestinal Differentiation," Biotechnology and Bioengineering, vol. 111, No. 6: 1222-1232 (Jun. 2014).

Crank et al., "The Mathematics of Diffusion," Clarendon Press: 421 pages (1979).

Crosnier et al., "Organizing cell renewal in the intestine: stem cells, signals and combinatorial control," Nature Reviews Genetics, vol. 7: 349-359 (2006).

Cummings et al., "Properties of engineered vascular constructs made from collagen, fibrin, and collagen-fibrin mixtures," Biomaterials, vol. 25: 3699-3706 (2003).

Damink et al., "Glutaraldehyde as a crosslinking agent for collagen-based biomaterials," Journal of Materials Science: Materials in Medicine, vol. 6: 460-472 (1995).

(56) References Cited

OTHER PUBLICATIONS

Date et al., "Mini-Gut Organoids: Reconstitution of Stem Cell Niche." Annual Review of Cell and CDevelopmental Biology, vol. 31: 269-289 (2015).

Davie, "Inhibition of Histone Deacetylase Activity by Butyrate", Journal of Nutrition, vol. 133: 2485S-2493S (2003).

Dekkers et al., "A functional CFTR assay using primary cystic fibrosis intestinal organoids." Nature medicine, vol. 19: 939 (2013).

Deveney et al., "Establishment of Human Colonic Epithelial Cells in Long-Term Culture," Journal of Surgical Research, vol. 64: 161-169 (1996).

Deward et al., "Cellular heterogeneity in the mouse esophagus implicates the 30 presence of a nonquiescent epithelial stem cell population," Cell. Rep., vol. 9(2): 701-711 (Oct. 23, 2014).

Di et al. "Collagen stabilization and modification using a polyepoxide, triglycidyl isocyanurate," Polymer Degradation and Stability, vol. 94: 1684-1692 (2009).

Donohoe et al., "The Warburg Effect Dictates the Mechanism of Butyrate-Mediated Histone Acetylation and Cell Proliferation," Molecular Cell, vol. 48: 612-626 (2012).

Donohoe et al., "The Microbiome and Butyrate Regulate Energy Metabolism and Autophagy in the Mammalian Colon," Cell Metabolism, vol. 13, Issue 5: 517-526 (May 2011).

Eastwood et al., "Organ culture of human rectal mucosa," Gastroenterology, vol. 64(3): 375-382 (1973).

Elamin et al., "Effects of Ethanol and Acetaldehyde on Tight Junction Integrity: In Vitro Study in a Three Dimensional Intestinal Epithelial Cell Culture Model," PLoS One, vol. Vol. 7, Article ID e35008 (2012).

Elkins et al., "Mechanisms and applications of hypertonic saline." Journal of the Royal Society of Medicine, vol. 104: S2-S5 (2011).

Engelberg et al., "Mechanical and Thermal Properties of Epoxy Resins With Reversible Crosslinks," Polymer Engineering & Science, vol. 30: 303-307 (1990).

Eveillard et al., "Identification and characterization of adhesive factors of Clostridium difficile involved in adhesion to human colonic enterocyte-like Caco-2 and mucus-secreting HT29 cells in culture," Molecular microbiology, vol. 7: 371-381 (1993).

Fatehullah et al., "Cell and tissue polarity in the intestinal tract during tumourigenesis: cells still know the right way up, but tissue organization is lost." Philosophical Transactions of the Royal Society B-Biological Sciences, vol. 368: 20130014 (2013).

Faul et al., "G*Power 3: A flexible statistical power analysis program for the social, behavioral, and biomedical sciences," Behavior Research Methods, vol. 39: 175-191 (2007).

Ferruzza et al., "A protocol for differentiation of human intestinal Caco-2 cells in asymmetricserum-containing medium," Toxicology in Vitro, vol. 26: 1252-1255 (2012).

Fier et al., "Stem Cells, Self-Renewal, and Differentiation in the Intestinal Epithelium," Annu. Rev. Physiol, vol. 71: 241-260 (2009).

Finkbeiner et al., "Stem cell-derived human intestinal organoids as an infection model for rotaviruses," Mbio, vol. 3: e00159-12 (2012).

Formeister et al., "Distinct SOX9 levels differentially mark stem/ progenitor populations and enteroendocrine cells of the small intestine epithelium," Am. J Physiol.-Gastroint. Liver Physiol., vol. 296: G1108-G1118 (2009).

Franck et al., "Three-Dimensional Traction Force Microscopy: A New Tool for Quantifying Cell-Matrix Interactions," PloS one, vol. 6: e17833 (2011).

Frantz et al., "The extracellular matrix at a glance," Journal of Cell Science, vol. 123: 4195-4200 (2010).

Fuchs et al. "A matter of life and death: self-renewal in stem cells," Embo Reports, vol. 14, No. 1: 39-48 (2013).

Fung et al., "Butyrate-Induced Apoptosis in HCT 116 Colorectal Cancer Cells Includes Induction of a Cell Stress Response," Journal of Proteome Research, vol. 10: 1860-1869 (2011).

Gagnon et al., "Comparison of the Caco-2, HT-29 and the mucus-secreting HT29-MTX intestinal cell models to investigate *Salmonella* adhesion and invasion," Journal of Microbiological Methods, vol. 94: 274-279 (2013).

Galland, "The gut microbiome and the brain," Journal of Medicinal Food, vol. 17: 1261-1272 (2014).

Gamet et al., "Effects of short-chain fatty acids on growth and differentiation of the human colon-cancer cell line HT29," International Journal of Cancer, vol. 52: 286-289 (1992).

Gattazzo et al., "Extracellular matrix: a dynamic microenvironment for stem cell niche," Biochimica et Biophysica Acta (BBA)—General Subjects, vol. 1840: 2506-2519 (2014).

Gaudier et al., "Butyrate specifically modulates MUC gene expression in intestinal epithelial goblet cells deprived of glucose," Am J. Physiol Gastrointest Liver Physiol., vol. 287: G1168-G1174 (2004).

Gersemann et al., "Differences in goblet cell differentiation between Crohn's disease and ulcerative colitis," Differentiation, vol. 77: 84-94 (2009).

Gibson et al. "Isolation of Colonic Crypts That Maintain Structural and Metabolic Viability In Vitro," Gastroenterology, vol. 96: 283-291 (1989).

Goldszmid et al., "The price of immunity," Nature Immunology, vol. 13: 932-938 (2012).

Gonzalez S et al., "A 3D Culture System Enhances the Ability of Human Bone Marrow Stromal Cells to Support the Growth of Limbal Stem/Progenitor Cells," Stem Cell Res., vol. 16(2): 358-364 (2016).

Gracz et al. "Indentification, Isolation, and Culture of Intestinal Epithelial Stem Cells from Murine Intestine," Methods Mol Biol. (2012).

Gracz et al., "CD24 and CD44 Mark Human Intestinal Epithelial Cell Populations with Characteristics of Active and Facultative Stem Cells," Stem Cells, vol. 31(9): 2024-2030 (2013).

Gray et al., "Mucocillary differentation of serially passaged normal human tracheobronchial epithelial cells," American Journal of Respiratory Cell and Molecular Biology, vol. 14: 104-112 (1996).

Gross et al., "Calibration of misonidazole labeling by simultaneous measurement of oxygen tension and labeling density in multicellular spheroids," International journal of cancer, vol. 61: 567-573 (1995).

Gunasekara et al., "A Monolayer of Primary Colonic Epithelium Generated on a Scaffold with a Gradient of Stiffness for Drug Transport Studies." Analytical Chemistry, vol. 90: 13331-13340 (2018).

Gunawardene et al., "Classification and functions of enteroendocrine cells of the lower gastrointestinal tract: Classification and functions of colorectal enteroendocrine cells," International Review of Experiemental Pathology, vol. 92, No. 4: 219-231 (Aug. 31, 2011).

Hai-Long et al., "The Effect of Amino Density on the Attachment, Migration, and Differentiation of Rat Neural Stem Cells In Vitro," Mol Cells., vol. 35: 436-443 (2013).

Hall et al., "Human genetic variation and the gut microbiome in disease," Nature Reviews Genetics, vol. 18: 690 (2017).

Haller et al., "Non-pathogenic bacteria elicit a differential cytokine response by intestinal epithelial cell/leucocyte co-cultures." Gut, vol. 47: 79-87 (2000).

Hansson, "Role of mucus layers in gut infection and inflammation," Current Opinion in Microbiology, vol. 15: 57-62 (2012).

Hass et al., "Lack of Butyrate Is Associated With Induction of Bax and Subsequent Apoptosis in the Proximal Colon of Guinea Pig," Gastroenterology, vol. 112: 875-881 (1997).

Hayman et al., "Growth of human stem cell-derived neurons on solid three-dimensional polymers," Journal of Biochemical and Biophysical Methods, vol. 62: 231-240 (2005).

He et al., "Clostridium difficile toxin A triggers human coloncyte IL-8 release via mitochondrial oxygen radical generation." Gastroenterology, vol. 122: 1048-1057 (2002).

Hovakimyan et al., "Collagen Cross-Linking: Current Status and Future Directions," Journal of Ophthalmology, Article ID 406850 (2012).

Huang et al., "An insert-based enzymatic cell culture system to rapidly and reversibly induce hypoxia: Investigations of hypoxia-induced cell damage, protein expression and phosphorylation in neuronal IMR-32 cells," Disease models & mechanisms, vol. 6: 1507-1514 (2013).

(56) References Cited

OTHER PUBLICATIONS

Hubbi et al., "Regulation of cell proliferation by hypoxia-inducible factors," American Journal of Physiology—Cell Physiology, vol. 309: C775-C782 (2015).

In et al., "Enterohemorrhagic *Escherichia coli* reduces mucus and intermicrovillar bridges in human stem cell-derived colonoids," Cellular and molecular gastroenterology and hepatology, vol. 2: 48-62 e3 (2016).

Ito et al., "Metabolism and the control of cell fate decisions and stem cell renewal," Annual review of cell and developmental biology, vol. 32: 399-409 (2016).

Ivanovic, "Hypoxia or in situ normoxia: The stem cell paradigm," Journal of Cellular Physiology, vol. 219: 271-275 (2009).

Janshoff et al., "Cell Adhesion to Ordered Pores: Consequences for Cellular Elasticity," Journal of Adhesion Science and Technology, vol. 24: 2287-2300 (2010).

Janssenduijghuijsen et al., "Mitochondrial ATP Depletion Disrupts Caco-2 Monolayer Integrity and Internalizes Claudin 7," Frontiers in Physiology, vol. 8, Article 794: 13 pages (2017).

Janvilisri et al., "Transcriptional profiling of Clostridium difficile and Caco-2 cells during infection," The Journal of Infectious Diseases, vol. 202: 282-290 (2010).

Johansson et al., "Bacteria penetrate the normally impenetrable inner colon mucus layer in both murine colitis models and patients with ulcerative colitis." Gut, vol. 63: 281-291 (2014).

Johansson et al., "The inner of the two Muc2 mucin-dependent mucus layers in colon is devoid of bacteria," Proceedings of the National Academy of Sciences of the United States of America, vol. 105: 15064-15069 (2008).

Jones et al., "Inhibition of Histone Deacetylase Activity by Butyrate," Ecotoxicology, vol. 23: 802-808 (2014).

Jung et al., "Isolation and in vitro expansion of human colic stem cells," Nature Medicine, vol. 17: 1225-1227 (2011).

Kaidi, et al., "Interaction between β-catenin and HIF-1 promotes cellular adaptation to hypoxia," Nature Cell Biology, vol. 9: 210-217 (2007).

Kaiko et al., "Host-microbe interactions shaping the gastrointestinal environment," Trends in Immunology, vol. 35: 538-548 (2014).

Werlang et al., "Engineering mucus to study and influence the microbiome," Nature Reviews Materials, vol. 4: 134-145 (2019).

Whitcutt et al., "A biphasic chamber system for maintaining polarity of differentiation of cultured respiratory tract epithelial cells." In Vitro Cellular & Developmental Biology, vol. 24: 420-428 (1988).

Whitehead et al., "A method for the isolation and culture of human colonic crypts in collagen gels," In Vitro Cellular & Developmental Biology, vol. 23, No. 6: 436-442 (1987).

Whitehead et al., "Effects of short-chain fatty acids on a new human colon carcinoma cell line (LIM1215)," Gut, vol. 27: 1457-1463 (1986).

Wu et al., "Vasoactive Intestinal Polypeptide Promotes Intestinal Barrier Homeostasis and Protection Against Colitis in Mice." Plos One, vol. 10: e0125225 (2015).

Xu et al., "Butyrate induces apoptosis by activating PDC and inhibiting complex I through SIRT3 inactivation," Signal Transduction and Targeted Therapy, vol. 2: e16035 (2017).

Yang "Enhance physiocochemical properties of collagen by using EDC/NHS-crosslinking," Bull. Mat. Sci., vol. 35: 913-918 (2012).

Yen et al., "The gastrointestinal tract stem cell niche," Stem Cell Rev., vol. 2(3): 203-212 (2006).

Yeste et al., "Engineering and monitoring cellular barrier models," Journal of Biological Engineering, vol. 12, No. 18: 1-19 (Sep. 2018).

Yim et al., "Force-dependent cell signaling in stem cell differentiation," Stem Cell Research & Therapy, vol. 3: 41 (2012).

Yin et al., "Niche-independent high-purity cultures of Lgr5+ intestinal stem cells and their progeny," Nature Methods, vol. 11: 106-112 (2014).

Yokoyama et al., "Differentiation of gastric surface mucous cells (GSM06) induced by air-liquid interface is regulated partly through mitogen-activated protein kinase pathway." Journal of Gastroenterology and Hepatology, vol. 22: 2310-2315 (2007).

Yoo et al. "Effects of Schisandra Lignans on P-Glycoprotein-Mediated Drug Efflux in Human Intestinal Caco-2 Cells," Planta Med., vol. 73: 444-450 (2007).

Young, "The role of the microbiome in human health and disease: an introduction for clinicians," BMJ vol. 356: j831 (2017).

Yui et al., "Functional engraftment of colon epithelium expanded in vitro from a single adult Lgr5+ stem cell," Nature Medicine, vol. 18: 618-623 (2012).

Zeitouni et al., "The impact of hypoxia on intestinal epithelial cell functions: consequences for invasion by bacterial pathogens," Molecular and Cellular Pediatrics, vol. 3, No. 14 (2016).

Zheng et al., "Physiologic hypoxia and oxygen homeostasis in the healthy intestine: A review in the theme: Cellular Responses to Hypoxia," American Journal of Physiol cell Physiol, vol. 309: C350-C360 (2015).

Zhou et al., "Multifunctional bioreactor system for human intestine tissues," ACS Biomaterials Science & Engineering, vol. 4: 231-239 (2017).

Extended European Search Report corresponding to European Application No. 16744178.1, dated Jul. 2, 2018.

Extended European Search Report corresponding to European Patent Application No. 17835084.9, dated Mar. 5, 2020.

Extended European Search Report for U.S. Appl. No. 19/806,626 dated Feb. 4, 2022.

Extended European Search Report for U.S. Appl. No. 19/806,626 dated Feb. 28, 2022.

International Search Report and Written Opinion corresponding to International Application No. PCT/US2016/015631, dated May 26, 2016.

International Search Report and Written Opinion corresponding to International Application No. PCT/US2017/043601, dated Nov. 16, 2017.

International Search Report and Written Opinion corresponding to International Application No. PCT/US2019/032393, dated Jul. 23, 2019.

International Search Report and Written Opinion corresponding to International Application No. PCT/US2019/033955, dated Aug. 15, 2019.

International Search Report and Written Opinion corresponding to International Application No. PCT/US2019/061743, dated Feb. 11, 2020.

Japanese Office Action in JP Application No. 2022-559825, dated Apr. 1, 2025, 4 pages.

Japanese Office Action in JP Application No. 2024-033959 dated Jun. 10, 2025, 3 pages.

Canadian Office Action in CA Application No. 3052250 dated May 12, 2023, 4 pages.

Lock et al., "Mucus models to evaluate the diffusion of drugs and particles," Advanced Drug Delivery Reviews, vol. 124: 34-39 (2018).

Sontheimer-Phelps et al., "Human Colon-on-a-Chip Enables Continuous In Vitro analysis of Colon Mucus Layer Accumulation and Physiology," cellular and Molecular Gastroenterology and Hepatologyl, vol. 9, No. 3: 507-526 (2020).

5 mm

EDU/NUCLEI

100 μm

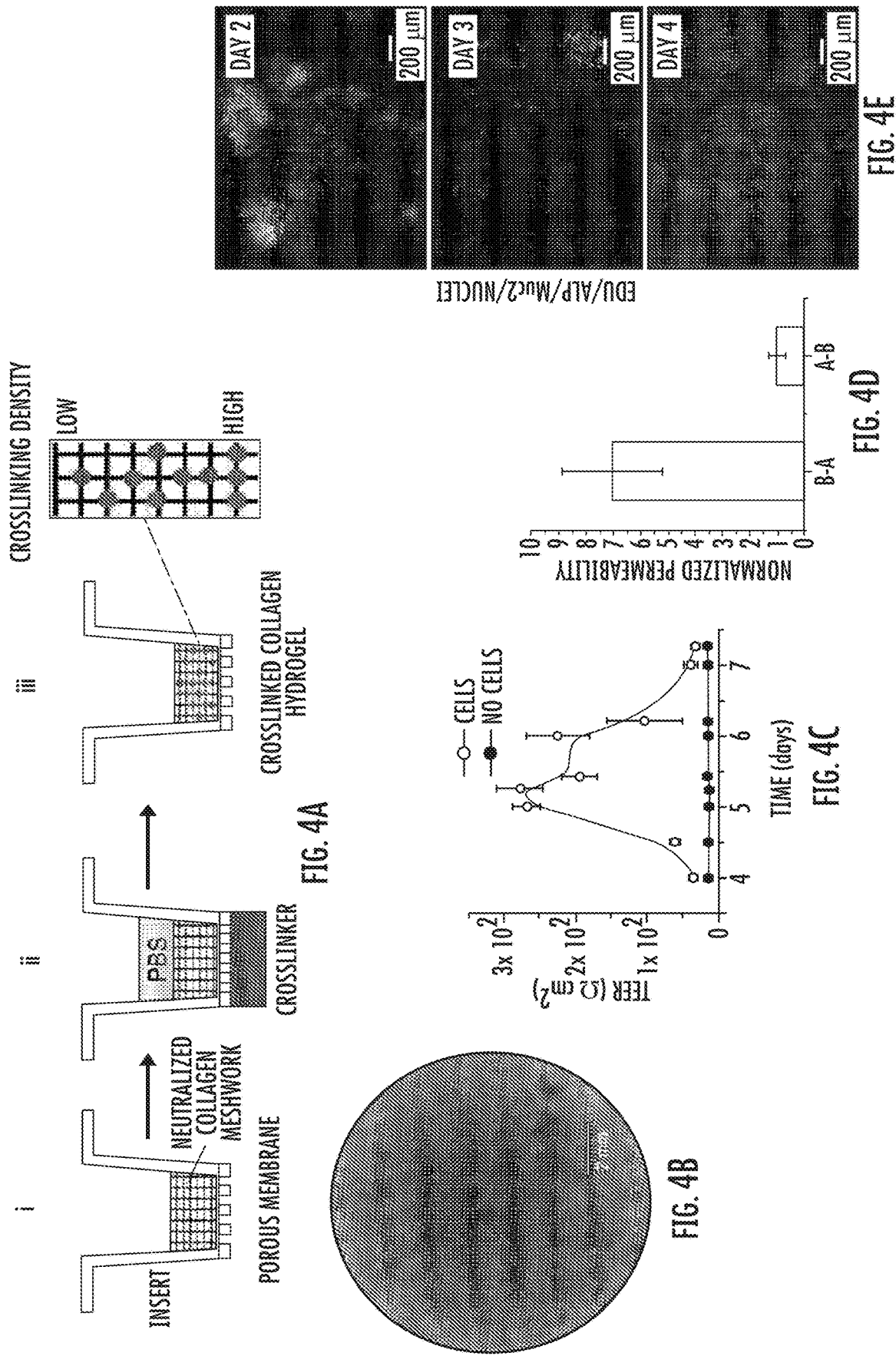

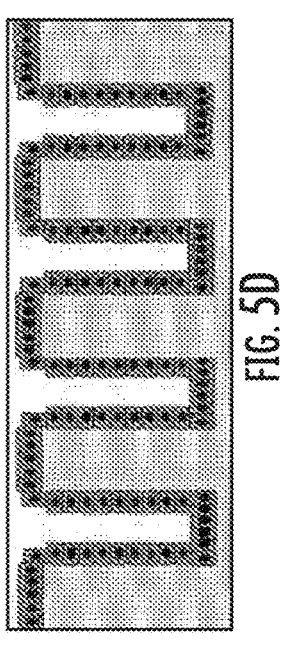
FIG. 5D
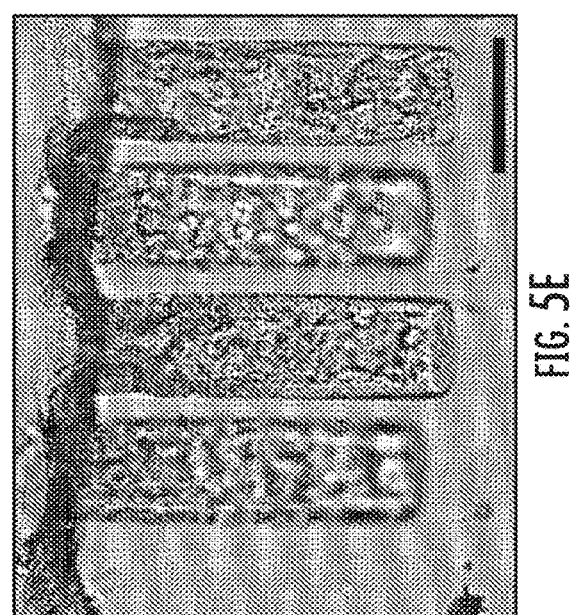
FIG. 5E
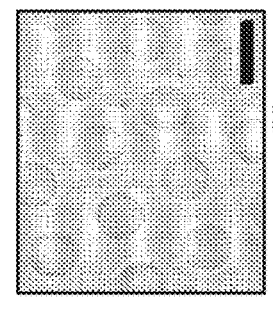
FIG. 5B
FIG. 5C
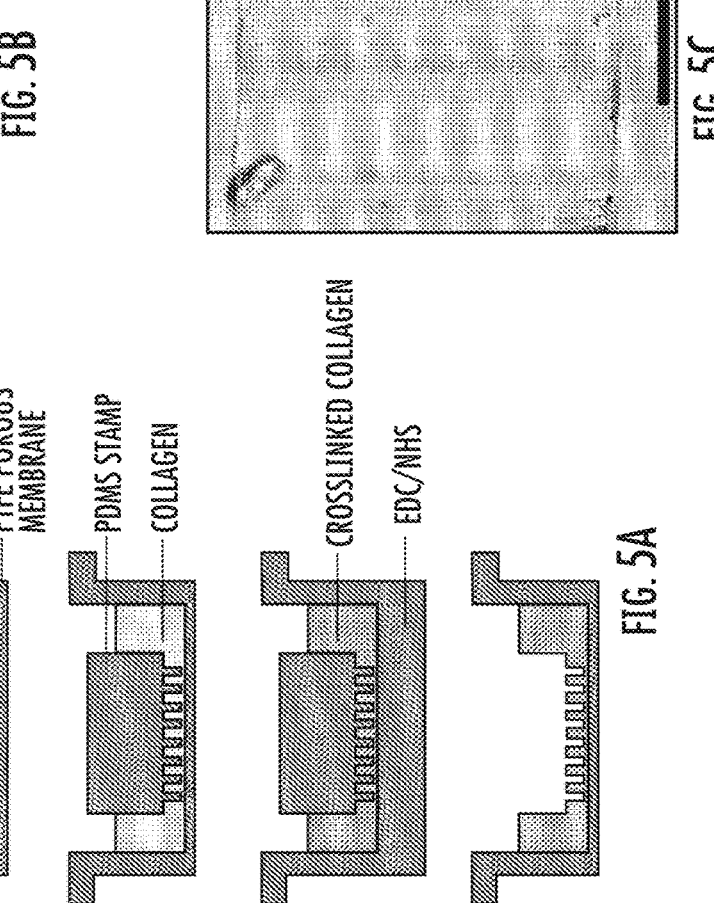
FIG. 5A

METHODS TO GENERATE POLYMER SCAFFOLDS HAVING A GRADIENT OF CROSSLINKING DENSITY

PRIORITY

This application is a continuation of and claims priority to co-pending U.S. patent application Ser. No. 18/220,535, filed on Jul. 11, 2023, which claims is a continuation of and claims priority to U.S. patent application Ser. No. 16/316, 139 filed Jan. 8, 2019, which is a 35 U.S.C. § 371 national phase entry of International Application No. PCT/US2017/043601, filed Jul. 25, 2017, which claims the benefit, under 35 U.S.C. § 119(e), of U.S. Provisional Application No. 62/367,339 filed on Jul. 27, 2016, the entire contents of each of which is incorporated by reference herein.

GOVERNMENT SUPPORT

This invention was made with Government support under Grant number DK109559 awarded by the National Institutes of Health. The United States Government has certain rights to this invention.

BACKGROUND

The small intestine and colon are lined with by single layer of epithelial cells possessing a rapid self-renewal rate (about 5 days in mice[1]) fueled by stem cells residing at the base of the intestinal crypts.[2] The stem cells are maintained in an in vivo microenvironment referred to as a stem cell niche which requires both biochemical and biophysical properties, including soluble factors (e.g. Wnt-3A, BMP and Notch) that vary along the basal-luminal axis, and biophysical interactions with a basement membrane.[3-5] In vitro culture of primary intestinal epithelial cells has been attempted since 1970s, but none of the attempts generated truly long-term proliferative, self-renewing cells. For example, standard 2D culture of intestinal cells in dishes only generated a short-term culture followed by the onset of apoptosis of cells.[13-15] This situation was rectified in 2009, when Hans Clevers and his colleagues reported a 3D organoid culture system that provided both biochemical (Wnt-3A, R-spondin, Noggin and epidermal growth factor [EGF]) and biophysical (Matrigel encapsulation) cues to the intestinal epithelial stem cells, to produce long-term proliferative culture of intestinal epithelial cells.[16-21] The cells grown under these conditions produce 3D structures referred to as organoids. Organoids contain self-renewing stem cells as well as the various differentiated intestinal lineages; goblet cells (secreting mucus), absorptive enterocytes (absorbing water and electrolytes), enteroendocrine cells (secreting hormones) and Paneth cells (small intestine).[18] While this 3D organotypic culture is effective in supporting long-term proliferative growth of organoids with all cell types, the system suffers from severe limitations. The major limitation is that the spheroidal architecture of the organoids is an obstacle in the study of molecular transport across the epithelial cells as the basal rather than luminal epithelial surface is exposed to exogenously added compounds. This reversal may be critical since metabolite-sensing GPCRs and other receptors are arrayed on the luminal surface, and molecular transport systems are directionally organized within the absorptive cells.[23]

SUMMARY

The present invention accordingly provides a method to strengthen a scaffold by diffusion of a crosslinker/strengthening reagents from one side of scaffold, instead of mixing them together. A benefit is to preserve the native property of scaffold at the top surface while effectively crosslinking or strengthening the scaffold at the bottom surface.

The scaffold may be collagen, particularly a collagen hydrogel. The hydrogel scaffold can be made from other materials, including natural and synthetic polymers. Examples of such materials include, but are not limited to, gelatin, laminin, agarose, chitosan, alginate, gelatinous protein mixture secreted by Engelbreth-Holm-Swarm (EHS) mouse sarcoma cells (e.g. Matrigel®), polyethylene glycol, polyacrylamide, etc.

The scaffold can be crosslinked by crosslinkers or strengthening reagents including covalent and non-covalent crosslinkers (for examples, ionic bonding, alginate can be gelled by calcium ions). Examples of crosslinkers include, but are not limited to, glutaraldehyde, ions (calcium), free radicals, ultraviolet, epoxy, N-hydroxysuccinimide esters, etc.

The invention provides methods of making a crosslinking gradient across a scaffold such as a collagen hydrogel; methods of making a stiffness gradient across a scaffold; methods of making a gradient of a protein of interest across a scaffold; methods of making a gradient of porosity (or meshwork openings) across a scaffold; and other objects and aspects as discussed further below.

Accordingly, an aspect of the invention is a method of making a live cell construct or a support, comprising: (a) providing a non-cellular organic polymer support having a top surface, a bottom surface, and an intermediate portion there between, (b) contacting a cross-linking agent to one surface of the support (e.g., under aqueous conditions) for a time sufficient to generate a gradient of cross-linking of the polymer in the intermediate portion; (c) optionally, wherein the gradient of cross-linking in the intermediate portion produces a corresponding gradient of free amino and/or carboxy groups in the intermediate portion, coupling a compound of interest to the free amino and/or carboxy groups to produce a gradient of the compound of interest in the intermediate portion; (d) optionally contacting live undifferentiated cells to the non-cellular support, and then (e) optionally propagating on the top surface an undifferentiated and/or differentiated cell monolayer (e.g., gastrointestinal epithelial cell monolayer (e.g., colon, small intestine, stomach, esophagus, tongue, nasopharnyx, oropharynx, laryngeopharynx, and/or pancreatic), urinary epithelial cell monolayer (e.g., kidney, bladder), respiratory epithelial cell monolayer (e.g., trachea, lungs), reproductive epithelial cell monolayer (e.g., testes, ovaries, ducts, endometrium), endocrine and endocrine gland epithelial cell monolayer (e.g., thyroid gland, adrenal glands, parathyroid glands, pancreas), lymph vessel epithelial cell monolayer, blood vessel epithelial cell monolayer, ventricular ependyma epithelial cell monolayer (e.g., brain, not neurons or astrocytes)).

In some aspects, the invention further provides a live cell construct, or a support useful for producing a live cell construct, comprising: (a) a non-cellular organic polymer support having a top surface a bottom surface, and an intermediate portion there between, the intermediate portion having a gradient of cross-linking of the polymer formed therein; (b) optionally, a monolayer of live undifferentiated and/or differentiated cells (e.g., gastrointestinal epithelial cell monolayer (e.g., colon, small intestine, stomach, esophagus, tongue, nasopharynx, oropharynx, laryngeopharynx, and/or pancreatic), urinary epithelial cell monolayer (e.g., kidney, bladder), respiratory epithelial cell monolayer (e.g., trachea, lungs), reproductive epithelial cell monolayer (e.g., testes, ovaries, ducts, endometrium), endocrine and endocrine gland epithelial cell monolayer (e.g., thyroid gland, adrenal glands, parathyroid glands, pancreas), lymph vessel epithelial cell monolayer, blood vessel epithelial cell monolayer, ventricular ependyma epithelial cell monolayer (e.g., brain, not neurons or astrocytes)) formed on the top surface; and (c) optionally, a gradient of (i) free reactive amino acid and/or carboxylic acid groups in the intermediate portion, or (ii) a gradient of a compound of interest covalently coupled to amino acid and/or carboxylic acid groups in the intermediate portion.

A further aspect of the invention provides a method of sustaining a live cell construct, comprising: (a) providing a construct as described above or below; (b) contacting a first culture medium to the top surface; and (c) contacting a second culture medium to the bottom surface, wherein one of the culture media induces the differentiation of propagating stem and progenitor cells and the other of the culture media induces the propagation of undifferentiated cells.

In some aspects, the invention provides a method of screening a test compound or microbe for a toxicological, physiological, or carcinogenic effect, comprising: (a) providing a construct as described above or below; (b) contacting a test compound or microbe to the construct; and then (c) detecting a toxicological, physiological, or carcinogenic effect of the microbe on the cells of the construct (e.g., by comparing the construct after the contacting to a like construct to which the compound or microbe has not been contacted, and/or by comparing the construct after the contacting step to the construct before the contacting step).

In some aspects, the invention provides a method of screening a test compound or microbe for a toxicological, physiological, or carcinogenic effect, comprising: (a) contacting a test compound or microbe to a live cell construct of the invention; and then (b) detecting a toxicological, physiological, or carcinogenic effect of the microbe on the cells of the construct (e.g., by comparing the construct after the contacting to a like construct to which the compound or microbe has not been contacted, and/or by comparing the construct after the contacting step to the construct before the contacting step).

In some embodiments of the foregoing, the support comprises a hydrogel.

In some embodiments of the foregoing, the cell monolayer has a surface area (e.g., a continuous uninterrupted surface area) of at least 0.01 or 0.1 square centimeters (e.g., up to 1 or 10 square centimeters, or more), and the cell monolayer has a resistance of at least 100, 150, or 200 Ohms per square centimeter (see P. Shah, V. Jogani, T. Bagchi, and A. Misra, Role of Caco-2 cell monolayers in prediction of intestinal drug absorption. Biotechnol. Prog. 22:186-198 (2006)).

In some embodiments of the foregoing, there is a gradient of porosity in the scaffold corresponding to the gradient of crosslinking (e.g., the gradient of porosity formed by the crosslinking process, with greater porosity (larger pores and/or more pores) being found in regions of less crosslinking, and lesser porosity (smaller pores and/or fewer pores) being found in the region of greater crosslinking The present invention is explained in greater detail in the drawings herein and the specification set forth below. Note that, while substantial discussion of embodiments with wells, crypts or lumens is provided, other embodiments of the invention do not require such wells, crypts or lumens. Note also that, while the invention is explained in substantial detail with embodiments where the epithelial cells are attached to the support, the epithelial cells can be detached from the support to provide a cell suspension thereof for other uses or purposes (e.g. therapeutics, implantation, drug screening, passage/expansion, cryopreservation, etc.).

BRIEF DESCRIPTION OF THE DRAWINGS

(FIG. 1A). Time-lapse images of crypts cultured on polystyrene (top panel) or a collagen hydrogel (bottom panel). Shown are overlaid brightfield and DsRed fluorescence images. Crypts were derived from a mouse expressing DsRed in all cells under a chicken-actin promoter. (FIG. 1B) Fluorescence images of cells at day 5 showing the EDU staining (shown here as light gray/white) and Hoechst 33342 (dark gray). Scale bar=100 μm in FIGS. 1A and 1B. (FIG. 1C) Ratio of EDU/nuclei for cells on polystyrene and the collagen hydrogel. (FIG. 1D) Low magnification brightfield (left) and fluorescence (right) images showing the cell-induced contraction of the collagen hydrogel (arrows). The primary murine colonic epithelial cells were plated on collagen hydrogel (1 mm height) inside a Falcon cell culture insert. The collagen hydrogel started to contract by day 2.

(FIG. 2A) Crosslinking of collagen chains by EDC/NHS coupling chemistry. (FIG. 2B) Crosslinking collagen by diffusing crosslinkers (EDC and NHS) from bottom. (i) Collagen solution was added to a cell culture insert with a porous membrane at its bottom. (ii) Crosslinking agents were added in the reservoir below the membrane. (iii) Diffusion of the crosslink agents acted on the collagen to generate a gradient in the density of crosslinking. (FIG. 2C) The degree of crosslinking density was visualized by fluorescence intensity in a cross-section slice of the hydrogel. This was accomplished by reacting residual amine groups of the hydrogel with a fluorescent amine-reactive dye, 5-carboxyfluorescein succinimidyl ester. (i) Fluorescence image of the cross-section of the hydrogel (thickness=1.8 mm) (ii) Fluorescence intensity profile.

(FIG. 3A) Wide-field fluorescence image showing the collagen hydrogel possessed a confluent cell layer without evidence of scaffold contraction. (FIG. 3B) Fluorescence images of cells showing the EDU staining (white/light gray) and Hoechst 33342 (dark gray). The cell culture time was 10 days for A and B. (FIG. 3C) TEER vs. time (n=3 scaffolds). (FIG. 3D) Basal-to-apical transport of rhodamine 123 and apical to basal diffusion of Lucifer yellow at day 9 of cell culture (n=3 scaffolds).

FIG. 4A-4E. Crosslinking collagen meshwork by diffusion of EDC/NHS, and the use of the crosslinked collagen hydrogel for culturing primary murine colonic epithelial cells. (FIG. 4A) Crosslinking strategy. (i) The collagen meshwork was prepared inside a cell culture insert. (ii) Crosslinkers (EDC and NHS) were added to a reservoir on the other side of the insert's membrane. (iii) Diffusion of crosslinkers crosslinked the collagen fibrils, generating a gradient of crosslinking density. (FIG. 4B) Wide-field fluorescence image showing the collagen hydrogel was fully covered with cells without scaffold contraction. (FIG. 4C) TEER vs. time (n=3 scaffolds). (FIG. 4D) Basal-to-apical (B-A) and apical-to-basal (A-B) transport of rhodamine 123 at day 5 of cell culture (n=3 scaffolds). (FIG. 4E) Different

Figures 1A, 1B, 1C, 1D:
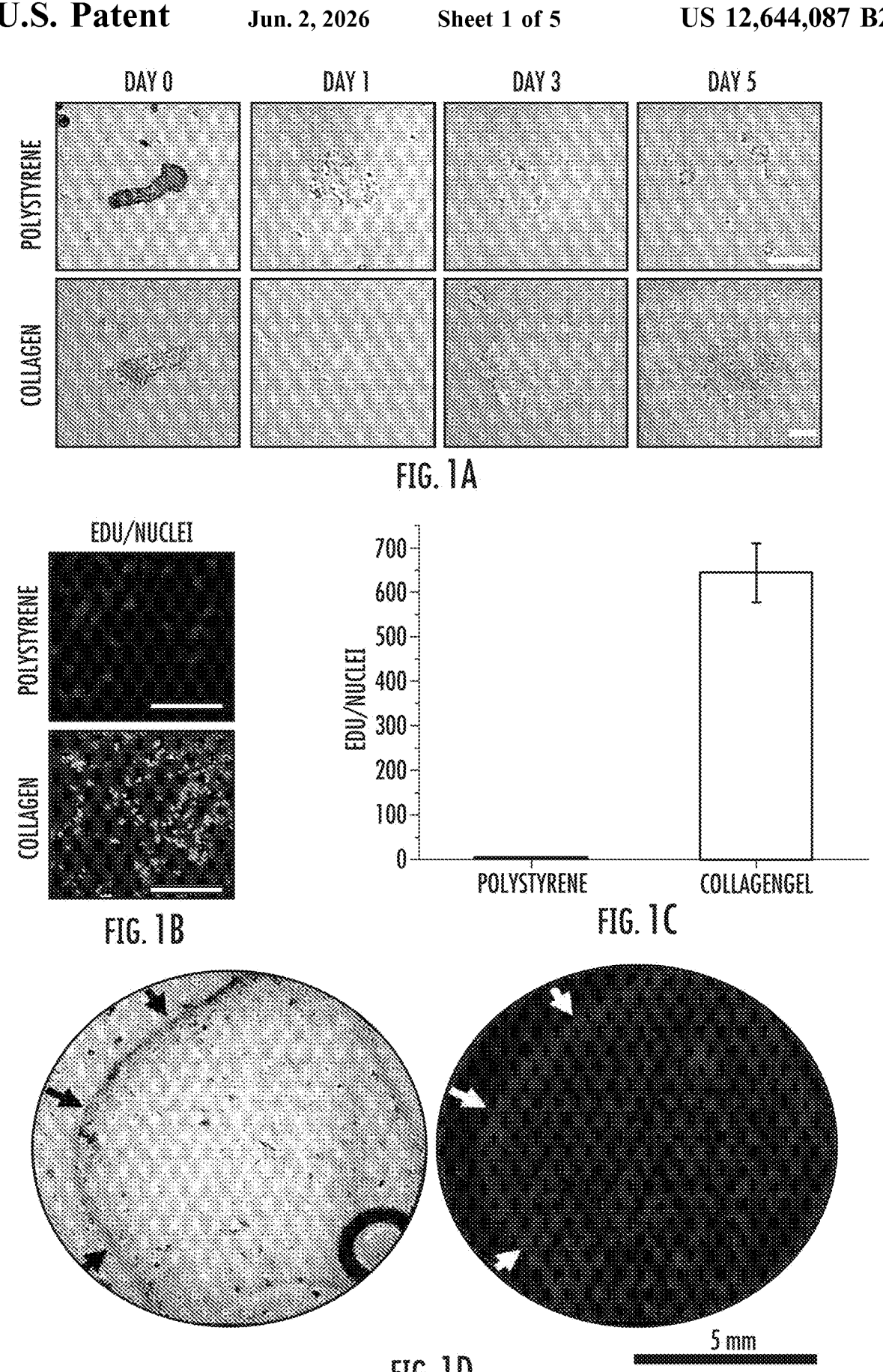
FIGS. 1A-1D. Collagen hydrogel maintained the proliferation of primary murine colonic epithelial cells, but its low strength was unsuitable for generating a continuous cell monolayer due to cell-induced contraction.

5 cell lineages in mouse 2D continuous monolayer over time. TEER of the same monolayer shown here=21 $\Omega cm^2$ (day 2), 117 $\Omega cm^2$ (day 3), and 880 $\Omega cm^2$ (day 4).

FIG. 5A-5E. 3D collagen scaffold generated by diffusing crosslinker from a reservoir underlying the Transwell insert/ hydrogel scaffold. (FIG. 5A) Schematic of fabrication process. (i) A Transwell insert with PTFE porous membrane. (ii) 200 μL collagen solution was added to the insert, followed by placing a PDMS stamp. (iii) Diffusion of EDC/NHS from the lower reservoir crosslinked the collagen. (iv) Release of the PDMS stamp generated a 3D collagen scaffold possessing an array of microwells (diameter=75 μm, height=250 μm, inter-well center-to-center gap=125 μm). (FIG. 5B) Top view of the 3D scaffold. (FIG. 5C) Side view of the 3D scaffold. (FIG. 5D) Schematic showing the 3D scaffold guides the cell growth to form in vitro crypts. (FIG. 5E) Brightfield image showing the in vitro crypt-like structures formed on the 3D scaffold from primary murine colonic epithelial cells. Scale bar=100 μm.

DETAILED DESCRIPTION

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

All publications, patent applications, patents and other references cited herein are incorporated by reference in their entireties for the teachings relevant to the sentence and/or paragraph in which the reference is presented.

Like numbers refer to like elements throughout. In the figures, the thickness of certain lines, layers, components, elements or features may be exaggerated for clarity. Where used, broken lines illustrate optional features or operations unless specified otherwise.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can have portions that overlap or underlie the adjacent feature.

Spatially relative terms, such as "top," "bottom," "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the present invention. The sequence of operations (or steps) is not limited to the order presented in the claims or figures unless specifically indicated otherwise.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The terms "contact" or "contacting" (or grammatical variations thereof) when used in reference to contacting a cell to a scaffold of the invention or contacting a test compound or microbe with a live cell construct of the invention refers to any means for delivering the cell to a scaffold of the invention, or the test compound or test microbe to a live cell construct of the invention.

1. Epithelial Cells

Cells such as undifferentiated cells and/or epithelial cells useful with the present invention may be of any species of origin, including, but not limited to, mammalian, avian, reptile, amphibian, and insect. In some embodiments the cells may be mammalian cells, examples of which include, but are not limited to, epithelial cells from human, monkey, ape, goat, sheep, dog, cat, horse, cow, and pig. In some embodiments, the cells may be derived from primary tissues, and in some embodiments, the cells are not cancer or tumor cells. Any type of epithelial cell from any organ comprising epithelial cells may be used, including, but not limited to, gastrointestinal epithelial cells, urinary epithelial cells, respiratory epithelial cells, reproductive epithelial cells, endocrine and endocrine gland epithelial cells, lymph vessel epithelial cells, blood vessel epithelial cells, ventricular ependyma epithelial cells.

In some embodiments, a gastrointestinal epithelial cell may be obtained from, for example, the colon, the small intestine, the stomach, the esophagus, the tongue, the nasopharynx, the oropharynx, the laryngeopharynx, and/or the pancreas. In some embodiments, a urinary epithelial cell may be obtained from, for example, the kidney or the bladder. In some embodiments, a respiratory epithelial cell may be obtained from, for example, the trachea or the lungs. In some embodiments, a reproductive epithelial cell may be obtained from, for example, the testes, the ovaries, the ducts, the endometrium. In some embodiments, an endocrine and endocrine gland epithelial cell may be obtained from, for example, the thyroid gland, the adrenal gland, the parathyroid gland, or the pancreas. In some embodiments, a ventricular ependyma epithelial cell may be obtained from the brain, but does not include neurons or astrocytes.

The epithelial cells may be undifferentiated cells (e.g., stem or progenitor cells), differentiated cells (e.g., enterocytes, Paneth cells, enteroendocrine cells, tuft cells, microcells, intra-epithelial lymphocytes, and/or goblet cells), or combinations thereof, depending upon the particular stage or time at which the invention is being carried out.

Epithelial cells, including undifferentiated epithelial cells (e.g., gastrointestinal epithelial cells, urinary epithelial cells, respiratory epithelial cells, reproductive epithelial cells, endocrine and endocrine gland epithelial cells, lymph vessel epithelial cells, blood vessel epithelial cells, ventricular ependyma epithelial cells) are known and may be harvested or provided in accordance with known techniques, or variations thereof that will be apparent to those skilled in the art. See, e.g., T. Yen and N. Wright, The gastrointestinal tract stem cell niche, Stem Cell Rev. 2(3), 203-212 (2006); S. Umar, Intestinal Stem Cells, Curr. Gastroenterol Rep. 12(5), 340-348 (October 2010); P. Jung et al., Isolation and in vitro expansion of human colonic stem cells, Nature Medicine 17, 1225-1227 (2011); J. Mills and R. Shivdasani, Gastric epithelial stem cells, Gastroenterology 140(2), 412-424 (February 2011); A. DeWard, J. Cramer, and E. Lagasse, Cellular heterogeneity in the mouse esophagus implicates the presence of a nonquiescent epithelial stem cell population, Cell. Rep. 9(2), 701-711 (Oct. 23, 2014); A. Gracz et al., CD24 and CD44 Mark Human Intestinal Epithelial Cell Populations with Characteristics of Active and Facultative Stem Cells, Stem Cells 31(9), 2024-30 (2013); F. Wang et al., Isolation and Characterization of Intestinal Stem Cells Based on Surface Marker Combinations and Colony-Formation Assay Gastroenterology 145(2), 383-95 (2013).

2. Supports, Live Cell Constructs and Methods of Making

As noted above, the present invention provides live cell constructs and supports and methods of making the same. In general, the methods are carried out by:

(a) providing a non-cellular support having a top surface and a bottom surface, (b) contacting live undifferentiated cells (e.g., stem and/or progenitor cells) to the non-cellular support (typically on the top surface thereof), and then (c) propagating a epithelial cell monolayer on support (typically on the top surface thereof).

The undifferentiated cells may be of any suitable type, including but not limited to mesenchymal stem cells, hematopoietic stem cells, induced pluripotent stem cells, stem cells obtained from or derived from, without limitation, gastrointestinal epithelia, urinary epithelia, respiratory epithelia, reproductive epithelia, endocrine and endocrine gland epithelia, lymph vessel epithelia, blood vessel epithelia, and/or ventricular ependyma epithelia.

The live cells in the monolayer may comprise both differentiated cells (e.g., enterocytes, Paneth cells, enteroendocrine cells, tuft cells, microcells, intra-epithelial lymphocytes, and/or goblet cells) and undifferentiated cells (e.g., stem or progenitor cells) in combination (e.g., in a ratio of from 1:10,000, 2:10,000, or 10:10,000, up to 10,000:1, or 10,000:10). In some embodiments, the method may further include the step of:

(d) contacting a culture media to the monolayer of live cells (e.g., which culture media is in or on the support), which culture media sustains the monolayer of live cells. In some embodiments, the culture media may include a short-chain fatty acid (e.g., butyrate, acetate, propionate, valproate, etc.), at a physiologic concentration (e.g., in the range of 0.1-5 mM for the colon). The culture media may also include typical nutrients, growth factors, and signaling factors and the like as discussed further below.

In some embodiments: (i) the culture media contains not more than 10 milliMolar of monosaccharides plus disaccharides (total, in combination); and, at the same time, (ii) the culture media may contain at least 2 milliMolar of said short chain fatty acids (e.g up to 20, or 100 milliMolar of short chain fatty acids total, in combination).

Advantageously, the monolayer may be sustained and propagated for an extended time. No upper limit for the length of time has been observed. For example, the monolayer may be sustained and propagated for a time of at least 2, 3, 4, 5, 6 or 7 days, 2, 3 or 4 weeks, or 2, 3, 4, 5, 6, 7, 8, 9, 10, 11, 12, 13, 14, 15, 16, 17, 18 months, 2 years, 3 years, or more. Thus in some embodiments, the monolayer may be sustained and propagated from about 1 day to about 2 years, about 1 week to about 2 years, about 1 month to about 2 years, about 6 months to about 2 years, about 1 week to about 2 months, about 1 week to about 4 months, about 1 week to about 6 months, about 1 month to about 4 months, about 1 month to about 6 months, about 1 month to about 9 months, about 1 month to about 1 year, about 1 month to about 18 months, about 1 month to about 2 years, and any range or value therein.

Supports used in the present invention (sometimes referred to as the extracellular matrix or "ECM") are described in the examples below and the discussion below. The supports may be organic, inorganic, or a composite thereof. In some embodiments the supports comprise an organic polymer such as collagen, typically in combination with other ingredients as discussed below. In many embodiments the supports are porous. The support may be provided or mounted on a porous carrier (e.g., a porous membrane, a mesh, an inorganic grid, a hydrogel, or a combination thereof) to lend structural support thereto, as also discussed below. The support may be in any suitable shape or configuration, including flat, tubular, curved, spherical, ellipsoid, etc., including composites there (e.g., to emulate macroanatomical structures).

Crosslinking of organic polymer supports. As noted above, in some embodiments of the present invention, the support comprises an organic polymer which may be crosslinked.

Any suitable crosslinking agent may be used to carry out the present invention, alone or in combination with one another. Numerous examples, and conditions for carrying out such crosslinking reactions, are known. See, e.g., U.S. Pat. Nos. 9,283,301; 9,272,004; 9,200,676; 9,211,362; 9,205,172; 9,132,208; 9,040,665; and 8,946,305.

The cross-linking agent may create covalent or non-covalent (e.g. ionic) cross-linking bonds. Examples of non-covalent crosslinking agents include ions such as calcium ions. Particular examples of crosslinking agents include, but are not limited to, carbodiimide (CBD; e.g. 1-Ethyl-3-(3-dimethylaminopropyl) carbodiimide or "EDC"; dicyclo-hexyl-carbodiimide or "DCC", etc.), N-hydroxylsuccinimide ester (NHS-ester), isothiocyanate, isocyanate, acyl azide, sulfonyl chloride, aldehyde, glyoxal, epoxide, oxirane, carbonate, aryl halide, imidoester, carbodiimide, anhydride, and/or fluorophenyl ester crosslinking agents, and any combination thereof.

Photosensitizer crosslinking agents. In some embodiments, the crosslinking agent may be a photosensitizer, which absorbs light radiation (e.g., ultraviolet light) and in turn leads to crosslinking of the scaffold. For example, ultraviolet light can crosslink a collagen support when the riboflavin is used as the crosslinking agent/photosensitizer (See, e.g., G. Wollensak et al., Riboflavin/ultraviolet-a-induced collagen crosslinking for the treatment of keratoconus. Am J Ophthalmol. 2003 May; 135(5): 620-7). In some embodiments, riboflavin absorbs UV radiation and generates reactive oxygen species and free radicals, which causes the crosslinking of collagen (e.g., a collagen hydrogel). For example, a gradient of crosslinking density can be created by placing riboflavin at the bottom of collagen hydrogel. Riboflavin diffuses into hydrogel and a gradient of riboflavin is established along the z-axis of the hydrogel. When the hydrogel is exposed to UV radiation on the top side, a gradient of crosslinking density is created. In addition to riboflavin, examples of suitable photosensitizer crosslinking agents include, but are not limited to, fiboflavin, photofrin, sulfosuccinimidyl 6-(4'-azido-2'-nitrophenylamino) hexanoate, 4-acryloyloxy benzophenone, phenyl-(1-acryloyloxy)-cyclohexyl ketone, and/or 1-Hydroxy-cyclohexyl-phenyl-ketone (IRGACURE 184).

Supports with wells to facilitate the formation of lumens or crypts. In some embodiments, the support top surface has a plurality of wells formed therein, each of the wells having a top opening, side walls and a floor (and typically not extending entirely through the support). The epithelial cell monolayer may extend into the wells that is, onto the well side walls and (generally) floors, with the well top openings remaining open, to form open lumens (or "crypts") lined with cells in the wells.

In some embodiments, the wells may be from about 100 to about 1000 microns deep or more (e.g., about 100, 150, 200, 250, 300, 350, 400, 450, 500, 550, 600, 650, 700, 750, 800, 850, 900, 950, 1000 microns deep or more and any range or value therein), and/or the wells may be from about 10 to microns wide (e.g., about 200 about 10, 20, 30, 40, 50, 60, 70, 90, 100, 110, 120, 130, 140, 150, 160, 170, 180, 190, 200 microns wide or more and arty range or value therein). In some embodiments, at least about 10, 20, 30, 40, 50, 60, 70, 80, 100 of the wells are formed in the top surface. Any suitable number of wells may be formed on the top surface, but in some embodiments at least about 10 to about 100 wells may be formed (e.g., about 100, 150, 200, 250, 300, 350, 400, 450, 500, 550, 600, 650, 700, 750, 800, 850, 900, 950, 1000 wells and any range or value therein)), up to about 1,000 to about 10,000 or more wells may be formed (e.g., about 1000, 2000, 3000, 4000, 5000, 6000, 7000, 8000, 9000, 10000 or more wells), depending upon the particular use of the construct. Thus in some embodiments, the wells may be from 100, 200 or 300 microns deep, up to 800 or 1000 microns deep or more, and/or said wells are from 10 or 50 microns wide, up to 100 or 200 microns wide or more; and/or at least 10, 50, or 100 of said wells are formed in said top surface.

The wells may have any suitable geometry, including a square, rectangular, circular, or elliptical profile, or other composite thereof; may have vertical or sloped side walls, or a combination thereof; may have flat or rounded floors, or a combination thereof; etc.

With constructs such as described above, a gradient of the stem cells (and/or the differentiated cells, or types of differentiated stem cells) may be formed in the monolayer. This can be achieved by: (a) providing a construct as described above; (b) contacting a first culture media to the construct top surface; and (c) contacting a second culture media (different from the first culture media) to the construct bottom surface. In some embodiments, one of the culture media induces the differentiation of propagating stem and progenitor cells and the other of the culture media induces the propagation of undifferentiated cells (e.g., by inclusion of appropriate signaling factors, as discussed further below). In some embodiments, the gradient may be oriented or aligned with the well walls (e.g., with the ratio of stem cells to differentiated cells being greater at the bottom of the well than at the top, or vice versa), as discussed further below.

Other support materials. Besides collagen, other types of ECM's may be used to build a biomimetic scaffold of the invention. These include, but are not limited to, gelatin, laminin, elastin, fibronectin, heparin sulfate, chondroitin sulfate, keratin sulfate, hyaluronic acid, gelatinous protein mixture secreted by Engelbreth-Holm-Swarm mouse sarcoma cells (e.g. Matrigel®, Geltrex®, MaxGel™, etc.), and a mixture of the above ECMs (e.g. a collagen/Matrigel mixture). Hydrogel from natural polymers and synthetic polymers can also be used to build this scaffold, followed by surface engineering the scaffold with ECM molecules. Examples of natural polymers and synthetic polymers include chitosan, agarose, alginate, polyvinyl alcohol, sodium polyacrylate, acrylate polymers, polyethylene glycol, synthetic peptides, etc.

As noted above, the supports may also be inorganic, or a composite of organic and inorganic materials. Examples of inorganic materials suitable for supports include, but are not limited to, glass, hydroxyapatite, Bioglass such as 45S5 Bioglass, calcium phosphate, silicon, silicon oxide, titanium oxide, gold, aluminum oxide, etc. Where not inherently porous, these materials can be made porous by a variety of methods, including but not limited to sintering, etching, leaching, lithography, etc. For example, a porous mesh of silicon and gold can be fabricated by lithography/etching.

The supports or scaffolds of the invention may mimic or substantially mimic the biophysical microenvironment (lamina propria) in terms of the permeability, stiffness, and presence of ECM components. In some embodiments, the scaffolds may be fabricated from polymer hydrogel comprising about 51-100 wt % water (e.g., 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 wt %, and the like and any range or value therein) and about 0-49 wt % polymer (e.g, 1, 2, 3, 4, 5, 6, 7, 8, 9, 10, 11, 12, 13, 14, 16, 17, 18, 19, 20, 21, 22, 23, 24, 25, 26, 27, 28, 29, 30, 31, 32, 33, 34, 35, 36, 37, 38, 39, 41, 42, 43, 44, 45, 46, 47, 48, 49 wt %, and the like and any range or value therein). Thus, in some embodiments, polymer hydrogel may comprise about 60 wt % water and about 40 wt % polymer, about 65 wt % water and about 35 wt % polymer, about 70 wt % water and about polymer, about 75 wt % water and about 25 wt % polymer, about 80 wt % water and about 20 wt % polymer, about 85 wt % water and about 15 wt % polymer, about 90 wt % water and about 10 wt % polymer, about 91 wt % water and about 9 wt % polymer, about 92 wt % water and about 8 wt % polymer, about 93 wt % water and about 7 wt % polymer, about 94 wt % water and about 6 wt % polymer, about 95 wt % water and about 5 wt % polymer, about 96 wt % water and about 4 wt % polymer, about 97 wt % water and about 3 wt % polymer, about 98 wt % water and about 2 wt % polymer, about 99 wt % water and about 1 wt % polymer, about 99.5 wt % water and about 0.5 wt % polymer, about 99.9 wt % water and about 0.1 wt % polymer, about 99.9 wt % water and about 0.01 wt % polymer, and any range or value therein. In some embodiments, the polymer hydrogel comprises the polymer in the range of about 0.01-10 wt % and water in the range of about 90-99.99 wt %. In some embodiments, the hydrogel may be a collagen hydrogel and the polymer may be in the range of about 0.01-10 wt % and the water may be in the range of about 90-99.99 wt %.

The polymer may include natural polymers (e.g. collagen, gelatin, Matrigel, laminin, chitosan, agarose, etc.) and/or synthetic polymers (polyethylene glycol, polyvinyl alcohol, etc.) The scaffolds may be fabricated from non-hydrogel materials that are tailored to have a layer of ECM proteins on their surface. The scaffolds may be porous or permeable to allow the passage of nutrients, factors, metabolites and other molecules. By virtue of this permeability, the tissue grown on such scaffolds may be subjected to gradients orthogonal to the plane of the tissue. Gradients may also be formed parallel to the surface of the tissue i.e. across the tissue surface. Perpendicular gradients across the 3D scaffolds maintain both stem cell and differentiated cells on the same scaffold by application of a gradient of growth factor across the scaffold. The scaffolds may be biodegradable to allow implantation for regenerative medicine applications. The scaffolds may be attached to a solid surface, or freestanding. The scaffold may be mixed with cellular materials (cells, tissues, blood, microbiota), or non-cellular materials (drugs, polymer beads, magnetic particles, etc.). In some embodiments, the addition of sodium butyrate to the medium may enhance the culture of colonic epithelial cells on the scaffolds. The tissue may be long-lived as the stem cells provide the source for self-renewal. The 3D scaffolds may contain microstructures (e.g. microwells, microposts, channels, stripes and other microstructures). The methods may be extended beyond colonic epithelium to other healthy gastrointestinal (GI) epithelial tissues (including small intestine, stomach, esophagus, tongue, pancreas, etc.), and to non-GI tissues possessing stem cells (liver, brain, hair follicle, kidney, retinal epithelium, etc.), as well as the diseased tissues.

Other factors, chemicals and drugs that can be used to form or impact crypts in vitro or alter their function. Gradients in signaling of factors (Wnt, BMP [bone morphogenic protein], and Notch) are thought to participate in crypt polarity by regulating cell position and proliferation. Besides the gradient of Wnt-3A proteins described above, other factors, small molecules and drugs may be used to regulate the cell signaling pathways to induce the polarization of tissues. The factors, small molecules and drugs can include, but are not limited to, activators and inhibitors of Wnt, BMP, GREM1,2, Notch signaling pathways. Examples are CHIR99021 (Wnt activator), IWP (Wnt inhibitor), Y-27632 (Notch inhibitor), Noggin (BMP inhibitor), Jagged 1 (Notch activator), Gremlin (BMP antagonist), cytokines, dietary compounds (fiber, butyrate, other fatty acids, metabolites), etc. Other fatty acids include propionate and/or acetate, which are short-chain fatty acids produced by microbial fermentation of fiber. Additional metabolites include, but are not limited to, branched chain fatty acids, bile acids and microbial-derived secondary bile acids, urea, amines, ammonia, lactate, phenols, indoles, sulfurs, carbon dioxide, hydrogen, hydrogen sulfide, and/or methane. Metabolites may include those from complex carbohydrates (soluble fiber), beans, and resistant starches, and can be produced from microbiota. Other chemicals useful with this invention include antidiuretic hormone, laxatives, bacterial endotoxins, hormones (e.g., VIP), and endogenous substances (e.g., bile acids), aldosterone, somatostatin, alpha2-adrenergic agents (e.g., clonidine), acetylcholine, nitric oxide, adenosine triphosphate (ATP), etc.

Other membranes may be used beneath the biomimetic scaffold. The biomimetic scaffolds can be fabricated on a support as described above. The supports include, but are not limited to, porous membrane (polytetrafluoroethylene [PTFE], polyester, polycarbonate, and/or cellulose), meshes (nylon, biodegradable polymers, metal), inorganic grit materials, and/or hydrogels, and others.

Other scaffolds can be used to support the long-term proliferative activity and viability of intestinal epithelial cells in the 2D monolayer. The scaffolds can mimic the biophysical microenvironment (lamina propria) in terms of the permeability, stiffness, and presence of ECM compo- nents. The scaffolds can be fabricated from polymer hydro- gel that may comprise about 51-100 wt % water and about 0-49 wt % polymer. The polymer may include natural polymers (e.g. collagen, gelatin, Matrigel, laminin, chitosan, agarose, etc.) and/or synthetic polymers (polyethylene gly- col, polyvinyl alcohol, etc.). The scaffolds may be fabricated from non-hydrogel materials that are tailored to have a layer of ECM proteins on their surface. In some embodiments, the scaffolds may be porous or permeable to allow the passage of nutrients, factors, metabolites and other molecules. The scaffolds may be biodegradable to allow implantation in bodies. The scaffolds may be attached to a solid surface, or freestanding. The scaffolds may be mixed with cellular materials (immune cells or other cell types, tissues, blood), or non-cellular materials (drugs, polymer beads, magnetic particles, etc.). Addition of a short-chain (e.g., C1 to C4 or C6) fatty acid such as sodium butyrate to the medium may enhance the culture of colonic epithelial cells on the scaf- folds. In some embodiments, the 3D scaffold may maintain both the stem cell and differentiated cells on the same scaffold by applying a gradient of growth factor across the scaffold. The tissue may be long-lived as the stem cells provide the source for self-renewal. The 3D scaffolds may contain microstructures (e.g. microwells, microposts, chan- nels, stripes and other microstructures). The methods of the invention may be extended beyond colonic epithelium to other healthy gastrointestinal (GI) epithelial tissues (includ- ing small intestine, stomach, esophagus, tongue, etc.), and to non-GI tissues possessing stem cells (liver, brain, hair fol- licle, kidney, retinal epithelium, etc.), as well as the diseased tissues.

Compounds of interest for coupling to solid supports. As noted above, the gradient of cross-linking in the solid support may also create a corresponding gradient of uncross- linked, and hence free, amino and/or carboxy groups on the polymer. Such amino and/or carboxy groups may be utilized to couple a compound of interest to the solid support, with the compound of interest being coupled to the support in a corresponding gradient manner or configuration. Suitable coupling reactions are known in the art.

Any suitable compound of interest may be attached to the free amino or carboxy groups. Examples include, but are not limited to: (1) proteins, including growth factors such as epidermal growth factor, fibroblast growth factor, platelet derived growth factor, Wnt proteins, R-Spondin proteins, Noggin, etc; differentiation factors such as bone morpho- genic protein, transforming growth factor beta proteins, growth differentiation factor proteins, etc.; and extracellular matrix proteins and cell adhesive molecules, such as pro- teoglycans, collagen, elastin, fibronectin, laminin, RGD peptide, vitronectin, leukadherin 1, etc.; and the like. (2) peptides, including cytomodulatory peptides such as cell adhesion peptides (e.g., RGD sequences), immunomodula- tory peptides such as beta-casein (54-59), alpha lactalbumin (51-53), ACE inhibitors, bradykinin, etc; mineral binding peptides such as Ser(P)-Ser(P)-Ser(P)-Glu-Glu, etc.; antimi- crobial peptides such as lactoferrin fragments, defensins, etc; antioxidative peptides; vasoactive intestinal peptides such as VIP (Vasoactive Intestinal Peptide), PACAP Pitu- itary Adenylate Cyclase Activating Peptide, Peptide Histi- dine Isoleucine 27, Growth Hormone Releasing Hormone, Glucagon, Secretin, etc., and the like; and (3) metabolites (generally small monomeric organic compounds), including fatty acids such as butyrate, acetate, caproic acid, succinate, etc.; bile acids such as deoxycholate; flavenoids such as luteolin, quercitin, etc.; phytoestrogens such as daidzin, genistin, etc.; phenols such as tannic acid, gallic acid, etc.; stilbenes such as resveratrol, aglcones, etc.; curcuminoids such as demethoxycurcumin, etc.; chalconoids such as chal- cone, etc.; terpenoids such as isoprene, eucalyptol, etc.; carotenoids such as beta-carotene, etc.; phytosterols such as beta-sitosterol, etc.; and the like.

3. Utilities

The current in vitro models for most epithelial tissues still rely on the use of immortalized cell lines derived from tumors. For example, Caco-2 cells derived from a colon carcinoma are widely used in mimicking the intestinal epithelium.

Although these tumor cell lines can form a contiguous monolayer, their cancer phenotype poorly reflects normal tissue physiology or microarchitecture found in vivo. This issue points to one of the major challenges of an in vitro tissue model which is the use of primary cells derived from normal tissue to form systems more representative of in vivo organ systems.

The 3D organoid culture systems overcame this need for continual culture of cells derived from primary cells, but remain limited by the enclosed architecture of the spheroidal organoid and need to culture within a gelatinous layer as opposed to a standard open surface typical of traditional tissue culture systems (for example, this may be contrasted to Calvin Kuo's air-liquid interface cultures, which are comprised on all layers (i.e., epithelium and mesenchyme) that are grown on flat surfaces and have a polarized epithe- lium and an exposed luminal surface. The difference again is that they are not long-lived and growth and differentiation is random and uncontrolled to a certain extent.). This surface may be planar or convoluted but is characterized by having an open architecture unlike the organoids which are closed structures. By inventing a culture system characterized by an open architecture, the present invention has overcome the limitations of the organoid system making the culture of epithelial tissues composed of primary cells compatible with conventional tissue culture methods and current robotics used in automated, high-throughput culture and analysis platforms. The open architecture and permeable substrate make possible a culture of cells under gradients of soluble factors both parallel and orthogonal to the epithelial surface. The open architecture may enable assays of epithelial barrier function, absorption, and secretion not possible in enclosed systems. Interactions of the primary epithelium with over- lying bacteria and other components of a microbiome are also now possible. These ex vivo tissues may be created from a variety of species including mouse, pig, and human among others. Model systems developed from transgenic animals, genetically modified human stem cells (e.g. TALEN or CRISPR/cas), induced pluripotent stem cells and stem cells derived from animal and human organisms with particular diseases are other non-limiting examples of mate- rials that may be used to create these tissues. The ability to create these tissues from healthy and diseased sources and from cells of differing genetic backgrounds will be impor- tant for screening drugs, study of disease mechanisms, and study of basic biology. Addition of various other cell types (e.g., immune cells, fibroblasts, and others found co-existing with the particular epithelial tissue in vivo) co-cultured on or within the biomimetic scaffold will be valuable for understanding cell-cell interactions and the effect of drugs and metabolites on the tissue. We posit that the epithelial tissues generated on the biomimetic scaffolds using primary tissue are superior to the current cell models for study of epithelial tissues. Some examples follow but this list is not all inclusive.

1) In vitro model for physiologic studies (molecular transportation across the intestinal epithelial cells, induced enzymatic functions, interaction with bacteria);

2) Screening studies of drugs, biologics, toxins, mutagens, dietary compounds, pathogens, viruses, microbiota, etc.;

3) Screening studies of microbiota under controlled conditions (oxygen tension, drug exposure, dietary compounds, metabolites, etc.);

4) Disease models by using stem and primary cells derived from a translational animal models or human;

5) Pharmacological and pharmacokinetic models for screening including comprehensive dose-response profiles for drugs, dietary compounds, etc.;

6) In vitro models to study metabolism;

7) In vitro models for wound healing of epithelial tissue to maintain barrier function;

8) In vitro models for study bacteria-epithelium interaction;

9) Tissue engineering for implantation to repair damaged epithelium;

10) Personalized medicine by studies performed on specific genetic backgrounds and individual patients;

11) Performance of assays such as: absorption of water and electrolytes (sodium, chloride, protons, bicarbonate, potassium), and the salvage of unabsorbed nutrients;

12) Impact of mucous flow, movement, and production as well as diseases stemming from this such as in cystic fibrosis;

13) Assays of antidiarrheal agent;

14) Assays of opiates, and treatments for constipation, for example, laxatives; Assays of syn-, pre- and probiotic agents;

16) Assay of radiopaque and scintigraphic markers and their impact on epithelium;

17) Impact of immune cells and their products (antibodies and cytokines) on epithelium;

18) Assay of soluble and insoluble fiber and its impact on the epithelium;

19) Understanding response to and repair of epithelium in response to injury of any type;

20) Investigation of bacteria leading to pseudomembrane formation, for example, *Clostridium difficile;*

21) Screening for carcinogenic compounds;

22) Screening for biowarfare compounds;

23) Studies to prevent GI bleeding as a side effect of NSAID treatment;

24) Studies of the role of the immune system on epithelial integrity and disease (e.g. inflammatory bowel diseases, enteropathies, cancer, etc.);

25) Assays for radio- and chemotherapeutics and agents that ameliorate off-target effects;

26) Ex vivo tissue expansion.

While the above applications relate primarily to studies enabled by the planar in vitro tissue constructs, the constructs can be envisioned as a means to create new tissue for repair of damaged or diseased tissue in the body. For example, the 2D monolayer could be used for regenerative medicine as follows: stem cells could be obtained from biopsy of a patient with digestive epithelial damage (e.g. from inflammatory bowel disease). The stem cells could be expanded on the scaffold to generate a large number of proliferative cells. The cells can be detached from the culture vessel, and placed back to the same patient to repair the damaged epithelial tissue.

4. Screening Methods

Thus, as noted above, in some embodiments, the present invention provides a method of screening a test compound or microbe for a toxicological, physiological, or carcinogenic effect, comprising: (a) contacting a test compound or microbe to a construct of the invention; and (b) detecting a toxicological, physiological, or carcinogenic effect of said test compound or microbe on the cells of said construct (e.g., by comparing the construct after said contacting to a like construct to which said test compound or microbe has not been contacted, and/or by comparing the construct after said contacting step to said construct before said contacting step). In some embodiments, the present invention provides a method of screening a test compound or microbe for a toxicological, physiological, or carcinogenic effect, comprising: (a) providing a construct as described above; (b) contacting a test compound or microbe to said construct; and then (c) detecting a toxicological, physiological, or carcinogenic effect of said test compound or microbe on the cells of said construct (e.g., by comparing the construct after said contacting to a like construct to which said test compound or microbe has not been contacted, and/or by comparing the construct after said contacting step to said construct before said contacting step).

In some embodiments, a test compound may be an aromatic organic compound, an aliphatic organic compound, a mixed aromatic and aliphatic organic compound. For example, in some embodiments, a compound for screening may be a compound that is a natural product, prebiotic, probiotic, foodstuff, carcinogen, drug, drug metabolite, bacterial metabolite and/or toxin, irritant, soil compound, ingestible toxin, and the like.

In some embodiments, a test microbe may selected from the group consisting of gram negative bacteria, gram positive bacteria, yeast, and molds. For example, in some embodiments, the microbe may be a bacterium of a type found in the ordinary or healthy gut flora (or "microbiome") of a mammal In some embodiments, the mammal may be human. See, e.g., US Patent Application Publication No. US 20140093478. In some embodiments, the microbe may be an infectious organism including, but not limited to, clostridium, cholera, salmonella, shigella, worms (tape, pin, hook, etc), amoeba (giardia, etc), and the like. Thus in some embodiments, the microbe may be an enteric bacteria or pathogen, including both benign and infectious enteric bacteria and pathogens.

Suitable detection methods include, but are not limited to, immunohistochemistry, PCR for DNA, mRNA expression, RNA sequencing, transepithelial electrical resistance, transport assays (ion, compound, protein, etc.), secretion assays, electron microscopy, flow cytometry, mass spectrometry of supernatants or reservoirs, ELISA and radiochemistry assays of the same, fluorescence based sensors of the same, and microbe adhesion to the epithelial cells.

The present invention is explained in greater detail in the following non-limiting examples. While particular examples of colonic monolayers are given, it will be appreciated that monolayers from other types of epithelial cells from any organ that comprises epithelial cells as described herein can also be formed. In some embodiments, epithelial cells from the colon, small intestine, intestine, stomach, esophagus, tongue, nasopharynx, oropharynx, laryngeopharynx, pancreas, kidney, bladder, trachea, lungs, testes, ovaries, ducts of the reproductive tract, endometrium, thyroid gland, adrenal gland, parathyroid gland, ventricular ependyma and/or brain may be used in a like manner as described below or by variations of such techniques that will be apparent to those skilled in the art.

Hydrogels composed of collagen, or other proteins such as gelatin,[6] can be strengthened by a variety of established crosslinking approaches,[7] for example by using crosslinkers of glutaraldehyde,[8] poly (ethylene glycol) ether tetrasuccinimidyl glutarate,[9] transglutaminase,[10] N-ethyl-N'-[3-dimethylaminopropyl] carbodiimide/N-hydroxy succinimide (EDC/NHS),[11] polyepoxide,[12] and natural products such as genipin.[13] In this invention, EDC/NHS is used as an example to crosslink a collagen hydrogel. The method outlined here can apply to any of a variety of other crosslinking approaches, as well as to other hydrogels. EDC/NHS-based carbodiimide coupling has an unique advantage in its zero-length crosslinking, i.e., EDC/NHS activates carboxylic acid groups and facilitates their reaction with amine residues, resulting in the formation of an amide bond. EDC/NHS molecules are not incorporated into the collagen hydrogel, and they are leached out or removed from the scaffold after the crosslinking reaction. As a result, the EDC/NHS modified collagen scaffold is virtually free of cell toxicity.[14]

We attempted crosslinking the collagen hydrogels by incubation in 600 mM EDC and 150 mM NHS in 2-(N-morpholino) ethanesulfonic acid (MES) buffer (pH 5, 0.1 M) for 4 h per prior published protocol. In this experiment, the crosslinking solution was added to the reservoir above the matrix. However, the collagen scaffold crosslinked in this manner couldn't support the proliferation of the primary murine colonic epithelial cells when these cells were added to the surface of the scaffold (data not shown, >10 trials). The reason for the poor cell growth properties was hypothesized to be that EDC/NHS crosslinking increased the stiffness (before crosslinking $118\pm136$ Pa [n=69 measurements]; after crosslinking $2,302\pm1,411$ Pa [n=53]), and modified the RGD (Arg-Gly-Asp) and other recognition sequences for integrins that mediate cell adhesion (e.g. L-aspartic acid [Asp] has a carboxylic acid side group, which can be modified by EDC/NHS), thus making the modified hydrogel unsuitable for culturing the primary intestinal epithelial cells.

Figure 2A:
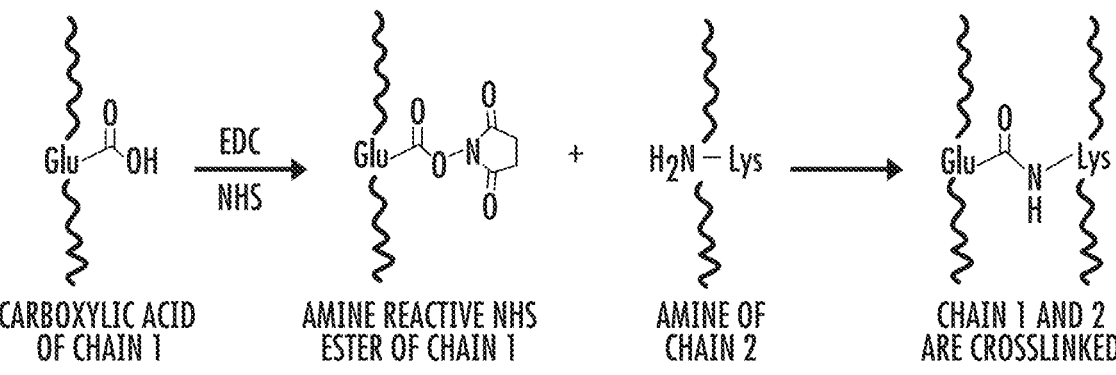
FIGS. 2A-2C. Collagen hydrogel scaffold possessing a gradient in crosslinking density.
Figure 2B:
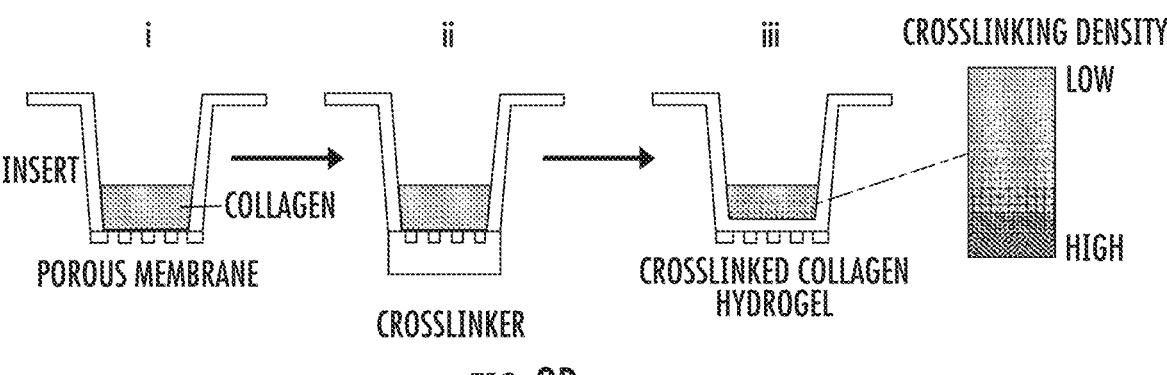
Figure 2C:
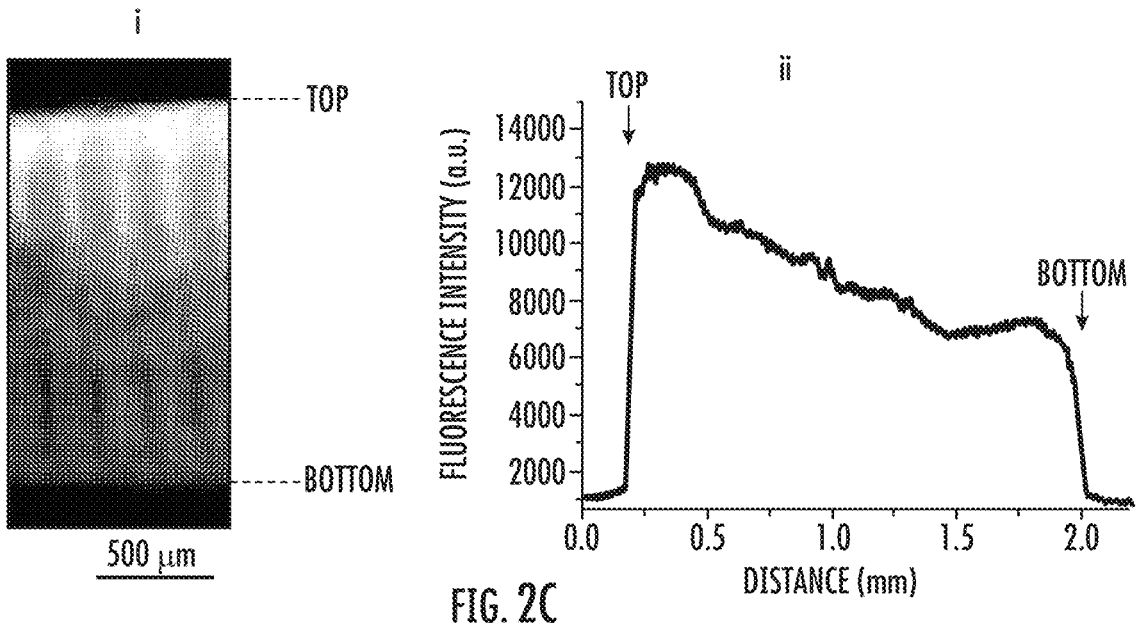

In this invention, we propose a novel method to strengthen the collagen hydrogel by diffusing a crosslinker, such as EDC/NHS, from one side of collagen hydrogel layer, thus generating a crosslinked collagen hydrogel possessing a gradient of crosslinking density along its thickness (FIG. 2). The gradient in crosslinking density was demonstrated by visualizing the fluorescence intensity of a cross-section of the hydrogel after reacting the residual amine groups of the hydrogel with a fluorescent amine-reactive dye (FIG. 2C). The crosslinked collagen hydrogel was found to be suitable for culturing primary intestinal epithelial cells as the result of a relatively low crosslinking density on the surface where cells were adhered, thus preserving the desired stiffness and molecular composition (i.e. the RGD cell adhesion motif). At the same time, cell-induced contraction of the bulk hydrogel was effectively prevented as the surface of the collagen in direct contact with the crosslinking solution possessed a relatively high crosslinking density. This novel method generates a collagen hydrogel with enhanced resistance to contraction without significantly changing the stiffness and molecular composition of its cell-culture surface. Three examples of crosslinking collagen using this diffusional crosslinking method are given here: (1) crosslinking collagen chains to generate a 2D planar hydrogel scaffold; (2) crosslinking neutralized collagen meshwork to generate a 2D planar scaffold; (3) crosslinking collagen to generate a 3D scaffold.

Example 1

Crosslinking Collagen Molecular Chains to Generate a 2D Planar Hydrogel Scaffold Possessing a Gradient of Crosslinking Density Both carboxylic acid and primary amine groups are abundant in collagen. For example, per 1,000 amino acid residues in mammalian skin collagen, there are 121 carboxylic acid groups (Glutamic acid: 74 residues/1000, Aspartic acid: 47 residues/1000) and 29 primary amine groups (Lysine: 29 residues/1000).[15] In the presence of EDC and NHS, the carboxylic acid group of one chain of collagen is converted to a reactive NHS ester, which subsequently reacts with a primary amine group of the other chain of collagen to form a stable amide bond, and covalently crosslinking the collagen (FIG. 2A). During reaction, EDC/NHS act to catalyze the crosslinking and are not incorporated into the collagen, thus the EDC/NHS can be leached from the collagen gel after the reaction. The crosslinking strategy has been used to prepare a biocompatible collagen hydrogel as a tissue substitute for corneal implantation.[16]

FIG. 2B shows our strategy to generate a collagen hydrogel possessing a gradient of crosslinking density. Lyophilized collagen (type I, rat tail) was dissolved in MES buffer (0.1 M, pH 5) at a concentration of 5 mg/mL Collagen solution (100-200 μL) was added to a cell culture insert (BD Falcon #353180, for a 12-well plate, transparent PET membrane, $1.6\times10^6$ pores/cm$^2$, FIG. 2B-i). The insert was placed on a 12-well plate, and 1 mL solution of 35.3 mM EDC and 8.8 mM NHS in MES buffer (0.1 M, pH 5) was added to the well (black solution in FIG. 2B-ii schematic) for 1 h. The crosslinkers (EDC and NHS) transited through the porous membrane from the well to the cell culture insert to contact the collagen solution. EDC and NHS initiated the crosslinking reaction as they diffused into the collagen solution. After 1 h, the collagen solution inside the insert became a hydrogel. A gradient of crosslinking density with higher crosslinking density nearest the EDC/NHS solution and lower density at the upper surface of the hydrogel layer (FIG. 2B-iii).

As shown in FIG. 2A, the EDC/NHS crosslinking reaction consumes the primary amino groups, for example, non-crosslinked collagen derived from bovine Achilles' tendon contains 26.7 primary amino groups per 1,000 amino acid residues.[17] Reaction with 9.03 mM EDC and 3.61 mM NHS in MES buffer (0.05 M, pH 5.4) reduces the primary amino groups to 21.5 (15 min reaction time), 18.1 (30 min) and 13.6 (240 min).[17] Therefore, the residual primary amino groups can be used to reveal the crosslinking density, i.e., the less the residual amino groups, the higher will be the crosslinking density. To do so, the crosslinked collagen hydrogel was incubated in 10 μg/mL 5-carboxyfluorescein succinimidyl ester (5-FAM-SE) in PBS for 16 h. 5-FAM-SE is a fluorescent amine-reactive dye, which reacts with residual primary amino groups and covalently attach to the collagen molecules. After leaching of unreacted 5-FAM-SE, a thin slice of the collagen hydrogel was cut with a razor blade, and its cross-section was inspected using a fluorescence microscope. A gradient of fluorescence intensity was observed along the cross-section of the collagen hydrogel. The intensity was higher on the surface that was at a distance from the EDC/NHS solution indicating lower crosslinking when compared with the surface adjacent to the catalysts which displayed a reduced fluorescence (FIG. 2C). These data confirm the expectation of a gradient of crosslinking density shown schematically in FIG. 2B.

Figure 3A:
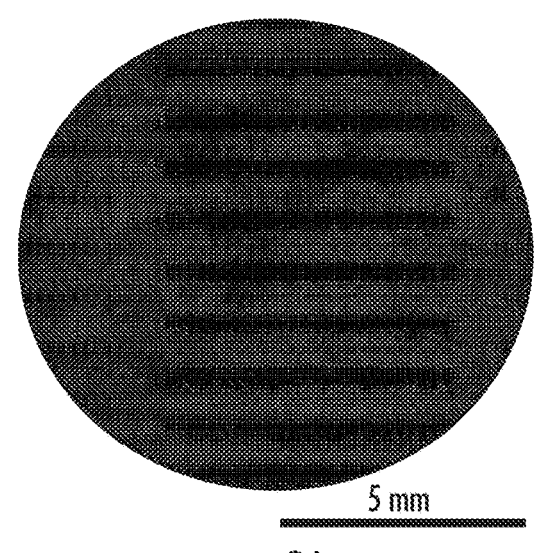
FIG. 3A-3D. Continuous monolayers of primary human small intestinal epithelial cells were generated on the cross-linked collagen hydrogel scaffold.
Figure 3B:
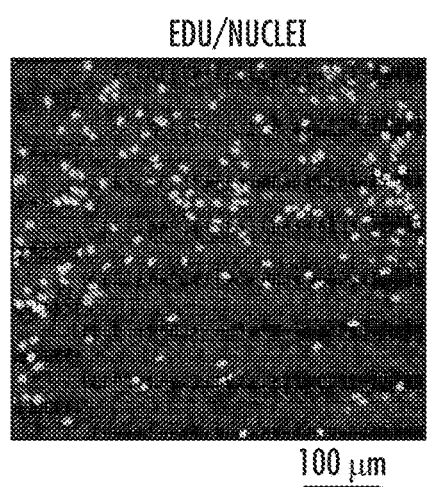
Figure 3C:
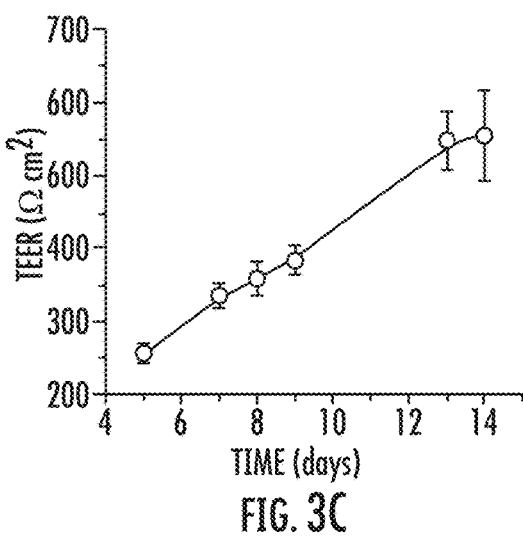
Figure 3D:
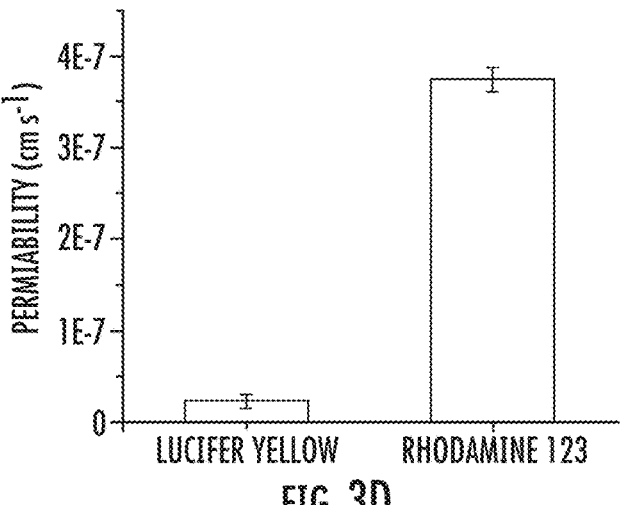

As the collagen surface on which cells are cultured has a relatively low crosslinking density, we hypothesized that the native stiffness and molecular composition (i.e. RGD motifs) are similar to unmodified collagen hydrogel, and thus will support the attachment and growth of primary intestinal epithelial cells. To test this hypothesis, human small intestinal epithelial cells were plated on a hydrogel scaffold prepared in this manner, and the cell growth and TEER were monitored for up to 14 days (FIG. 3C). The cells proliferated on the scaffolds, and no contraction of scaffolds was observed (n=3 scaffolds). The TEER increased over the 14 days in a linear fashion (FIG. 3C), reaching $555\pm62$ $\Omega\cdot cm^2$ (n=3) at day 14. At day 10, the cells were stained with EDU (3-h pulse) to assess proliferating cells and Hoecsht nuclear stain to enable assessment of cell coverage across the scaffold (FIGS. 3A and 3B). There was no contraction of the scaffold and 100% cell coverage was present. Proliferative cells (EDU$^+$) were distributed over the monolayer, indicating the scaffold supported cell proliferation. To demonstrate the functional utility of the gradient cross-linked scaffolds, basal-to-apical transport of a p-glycoprotein substrate (rhodamine 123) and permeability using a permeability marker (Lucifer yellow) were determined across the cell layer on the scaffold at day 9 at which time the TEER was $383\pm20$ $\Omega\cdot cm^2$ (n=3) (FIG. 3D). The permeability of rhodamine 123 ($37.4\pm1.3\times10^{-8}$ cm·s$^{-1}$, n=3) was 15 times higher than Lucifer yellow ($2.4\pm0.7\times10^{-8}$ cm·s$^{-1}$, n=3), demonstrating the active transport of rhodamine 123 facilitated by p-glycoprotein.

Example 2

Crosslinking a Collagen Meshwork by Unilateral Crosslinker Diffusion

In Example 1, we have shown the collagen peptide chains (solution at pH 5 in MES buffer) can be crosslinked by diffusion of EDC/NHS to generate a gradient of crosslinking density. Here we give another example by using a neutralized collagen meshwork. Collagen is soluble in water at acidic pH (pH≤5). Once its pH is adjusted to neutral (e.g. pH>7), collagen peptide chains start to become insoluble due to deprotonation of amine groups, precipitate and form self-assembled fibrils. Incubation at 37° C. facilitates the precipitation and formation of fibrils, generating a collagen hydrogel that is a meshwork of collagen fibrils. As shown in FIG. 1, this neutralized collagen hydro gel can support the proliferation of primary intestinal epithelial cells, but its has low mechanical strength because the collagen fibrils are not crosslinked. As discussed above, EDC/NHS can catalyze the crosslinking of adjacent collagen fibrils or fibril bundles by amide bonds resulting in a reduction of the swelling ratio and an increase in the resistance against thermal treatment and enzymatic degradation compared to non-crosslinked collagen hydrogel.[18]

We used a strategy outlined in FIG. 4A to crosslink a collagen meshwork by diffusing EDC/NHS from one side only. First, a neutralized collagen solution (1 mL, 1 mg/mL)

was prepared on ice by mixing collagen (295 μL of 3.39 mg/mL in 0.02 N acetic acid), sodium hydroxide (7 μL 1 N), HEPES (20 μL, 1 N, pH 7.4), sodium bicarbonate (60 μL, 7.5 wt %, pH 8), DI water (518 μL), and 10×phosphate buffered saline (PBS, 100 μL). The solution was mixed by slow and repeated pipetting. The mixture (200 μL) was added to a cell culture insert (BD Falcon #353180, for 12-well plate, transparent PET membrane, $1.6\times10^6$ pores/cm$^2$). The insert was incubated at 37° C. for 1 h to generate a collagen meshwork schematicaly illustrated as the black grid in FIG. 4A-i. To crosslink the collagen meshwork, the insert was placed on a 12-well plate, and 1 mL solution of 353 mM EDC and 88 mM NHS in PBS buffer was added to the well (solid gray region in FIG. 4A-ii), and 0.5 mL of PBS buffer was added to the insert (gray region in FIG. 4A-ii). Diffusion of the crosslinkers (EDC and NHS) through the porous membrane from the well to the cell culture insert. EDC and NHS initiated the crosslinking reaction as they diffused into the collagen meshwork, generating bridging amide bonds (represented as gray dots in FIG. 4A-iii). After a 40 min reaction, a gradient of crosslinking density was expected with higher crosslinking density on the side nearest the EDC/NHS solution and a lower density farther from the solution (FIG. 4A-iii).

To confirm the existence of a gradient of crosslinking density, we measured the stiffness of collagen meshworks using atomic force microscopy (AFM). Stiffness will be inversely proportional to crosslinking density. The neutralized collagen meshwork before crosslinking had a stiffness of $118\pm136$ Pa (n=69 measurements). The stiffness was increased to $2,302\pm1,411$ Pa (n=53 measurements) on the surface adjacent to the EDC/NHS solution. The stiffness of the opposite surface was increased to $1,159\pm572$ Pa (n=51 measurements), a value lying between non-crosslinked collagen (118 Pa) and the hydrogel adjacent to the crosslinking solution (2302 Pa). This result along with the previous fluorescence intensity data support the existence of a gradient of stiffness and crosslinking density along the height-layer of the collagen meshwork.

To test if the scaffold produced by the diffusionally generated neutralized collagen meshwork hydrogel was resistant to contraction during cell culture, primary murine colonic epithelial cells were plated on the collagen meshworks crosslinked by strategy shown in FIG. 4A. The collagen scaffold supported the proliferation of these cells. When the cell coverage reached 100%, none of the scaffolds had evidence of contraction (n=10 scaffolds, FIG. 4B). The TEER increased over time and reached at $2,682\pm208$ $\Omega\cdot cm^2$ (n=3) at day 5 (FIG. 4C). To identify cell proliferation and differentiation in these 2D monolayers a time series staining experiment was performed. As shown in the FIG. 4E, proliferative cells (EDU$^+$) in the monolayer differentiated largely to enterocytes (ALP$^+$) by day 3-4. Also, there are a few patches of goblet cells (Muc2$^+$) can also be seen in the monolayer (FIG. 4E). The subsequent decrease of TEER in FIG. 4C was likely the result of cell loss due to apoptosis of differentiated cells. To demonstrate the utility of these collagen meshwork hydrogel scaffolds, basal-to-apical (B-A) and apical-to-basal (A-B) transport of a p-glycoprotein substrate (rhodamine 123) were studied at day 5 when the TEER was >2,000 $\Omega\cdot cm^2$ (FIG. 4D). The permeability of rhodamine 123 from basal-to-apical was ~7-fold higher than apical-to-basal, indicating the active and directional transport of rhodamine 123 facilitated by p-glycoprotein.[19]

Example 3

3D Collagen Scaffold Generated by Unilateral Diffusion of the Crosslinker

Examples 1 and 2 have shown that planar, 2D collagen scaffolds can be crosslinked by diffusing EDC/NHS from one side of a collagen layer. Here, we show that a collagen scaffold possessing 3D microfeatures can be crosslinked by diffusing EDC/NHS in a similar manner. The 3D scaffold is useful in guiding cell proliferation to form in vitro tissues similar to in vivo intestinal crypts.

As discussed above, a major limitation of culture systems has been that the spheroidal architecture of the organoids presents an obstacle in the study of molecular transport across the epithelial cells. This is because the basal rather than luminal epithelial surface is exposed to exogenously added compounds.

To overcome this limitation, we screened a variety of scaffolds with a wide range of stiffness ($10^1$-$10^9$ Pa), and identified that neutralized collagen hydrogel (1 mg/mL, 1 mm height) can maintain the long-term proliferative culture of intestinal epithelial cells in a 2D monolayer with an accessible luminal surface as described in UNC patent application PCTUS2016015631. This 2D monolayer culture system recapitulates the 3D organoid system in terms of cell proliferation, differentiation, phenotypes and function. To exemplify the importance of the collagen hydrogel scaffold, colon crypts were plated at a density of 100 crypts/cm$^2$ on a polystyrene surface and a collagen hydrogel surface, respectively, in a medium containing all needed growth factors (Wnt-3A, R-spondin, Noggin and EGF, etc.). The cell growth was monitored up to 5 days (FIG. 1A). At day 5, the cell were stained with 5-ethynyl-2-deoxyuridine (EdU, for proliferative cells) and Hoechst 33342 (for nuclei of all cells), and the cell proliferation was quantified by the ratio of fluorescence intensity of EDU/nuclei (FIG. 1B and FIG. 1C). On a polystyrene surface, none of the crypts formed an expanding monolayer (FIG. 1A), and the proliferative cells (EDO were rare (FIGS. 1B and 1C). In contrast, cells formed an expanding monolayer on a collagen hydrogel and abundant proliferative cells (EDU$^+$) were present (FIGS. 1A, 1B and 1C). Cells of the monolayers on the collagen hydrogel were readily removed from the collagen surface with collagenase, disaggregated and sub-cultured. The cells could be maintained long-term (up to 10 months, the longest time tested to date) without loss of viability and proliferation capability. These data demonstrated that primary murine colonic epithelial cells were very sensitive to the biophysical properties of the scaffold, and the collagen hydrogel provided the biophysical cue to the stem cells by better mimicking the basement membrane underlying the intestinal epithelium in terms of stiffness (100-1,000 Pa), porosity, and presence of extracellular matrix (ECM) proteins. Although the neutralized collagen hydrogel maintained the proliferation of primary intestinal epithelial cells, its deficiency in mechanical strength proved a major weakness for its use in generating a contiguous cell monolayer. When the cell coverage was >70% over the surface of the hydrogel scaffold, the collagen hydrogel was seen to contract such that the scaffold curved up and detached from the sidewall of the culture device (100±0%, n=10 tests, FIG. 1D). As a result, a continuous cell monolayer covering the entire surface of the porous membrane could not be created. This produced leaking surrounding the cell layer through the porous membrane and prevented the creation of a contiguous monolayer capable of providing a transepithelial electrical resistance (TEER)>500 $\Omega \cdot$cm$^2$ as needed for transport and permeability studies (N=>50 attempts).

A PDMS stamp was first fabricated by standard photolithograhy followed by replica molding. The PDMS stamp possessed an array of cylindrical posts, with a height of 250 μm, a diameter of 75 μm, and a center-to-center gap of 125 μm. The PDMS stamp was plasma treated for 2 mM, followed by coating with mPEG-silane (1% in ethanol: water mixture [95:5 vol:vol], MW of mPEG-silane is 20,000) for 16 h. The PDMS stamp was rinsed with ethanol 5 times, and dried in air. Collagen solution (200 μL, 5 mg/mL in MES buffer [pH 5, 0.1 M]) was added to a cell culture Transwell insert (Corning #3460, for 12-well plate) with PTFE porous membrane, and the PDMS stamp was placed on the collagen (FIG. 5A-ii). The insert was placed on a 12-well plate, and the plate was placed in a pressurized pot at 25 psi of nitrogen for 5 min to remove trapped air bubbles among the PDMS posts. The nitrogen was slowly released from the pressure pot over about an 1 h. The plate was removed from the pressure pot, and 1 mL of a solution of 35.3 mM EDC and 8.8 mM NHS in MES buffer (0.1 M, pH 5) was added to the well (light gray region in FIG. 5A-ii) for 1 h. Diffusion of EDC and NHS through the porous membrane moved the crosslinkers from the well to the cell culture insert allowed the EDC and NHS to contact the collagen solution to initiate the crosslinking reaction. After 1-h crosslinking, the PDMS stamp was removed from the collagen layer, generating a 3D collagen scaffold (FIG. 5A-iv). The scaffold possessed an array of microwells with the same dimension as the PDMS posts (FIGS. 5B and 5C): the height of the microwell was 250 μm and the diameter was 75 μm. To demonstrate the 3D scaffold could be used to guide the intestinal epithelial cells to form in vitro intestinal crypt-like structures, primary murine colonic epithelial cells were plated on the scaffold and cultured. By day 4, the cells formed an array of 3D constructs whose tissue geometry was similar to colon crypts (FIGS. 5D and 5E). The collagen scaffold maintained the integrity and no contraction of deformation of the microwells was observed.

REFERENCES

1. N. Barker, M. van de Wetering and H. Clevers, Genes Dev., 2008, 22, 1856-1864.
2. E. Fuchs and T. Chen, Embo Reports, 2013, 14, 39-48.
3. M. Brittan and N. A. Wright, Gut, 2004, 53, 899-910.
4. C. Kosinski, V. S. W. Li, A. S. Y. Chan, J. Zhang, C. Ho, W. Y. Tsui, T. L. Chan, R. C. Mifflin, D. W. Powell, S. T. Yuen, S. Y. Leung and X. Chen, Proc. Natl. Acad. Sci. U.S.A., 2007, 104, 15418-15423.
5. T. H. Yen and N. A. Wright, Stem Cell Rev., 2006, 2, 203-212.
6. A. L. Paguirigan and D. J. Beebe, Nat Protoc, 2007, 2, 1782-1788.
7. M. Hovakimyan, R. F. Guthoff and O. Stachs, Journal of Ophthalmology, 2012, 2012, 406850.
8. L. Damink, P. J. Dijkstra, M. J. A. Vanluyn, P. B. Vanwachem, P. Nieuwenhuis and J. Feijen, Journal of Materials Science-Materials in Medicine, 1995, 6, 460-472.
9. N. Seyedhassantehrani, Y. Li and L. Yao, Integrative Biology, 2016.
10. J. M. Orban, L. B. Wilson, J. A. Kofroth, M. S. El-Kurdi, T. M. Maul and D. A. Vorp, Journal of Biomedical Materials Research Part A, 2004, 68A, 756-762.

11. N. E. Vrana, N. Builles, H. Kocak, P. Gulay, V. Justin, A. Malbouyres, F. Ruggiero, Damour and V. Hasirci, Journal of Biomaterials Science-Polymer Edition, 2007, 18, 1527-1545.

12. Y. Di and R. J. Heath, Polymer Degradation and Stability, 2009, 94, 1684-1692.

13. H. G. Sundararaghavan, G. A. Monteiro, N. A. Lapin, Y. J. Chabal, J. R. Miksan and D. I. Shreiber, Journal of Biomedical Materials Research Part A, 2008, 87A, 308-320.

14. E. Song, S. Y. Kim, T. Chun, H. J. Byun and Y. M. Lee, Biomaterials, 2006, 27, 2951-2961.

15. P. Szpak, J. Archaeol. Sci., 2011, 38, 3358-3372.

16. Y. W. Liu, L. H. Gan, D. J. Carlsson, P. Fagerholm, N. Lagali, M. A. Watsky, R. Munger, W. G. Hodge, D. Priest and M. Griffith, Invest. Ophthalmol. Vis. Sci., 2006, 47, 1869-1875.

17. P. B. van Wachem, J. A. Plantinga, M. J. B. Wissink, R. Beernink, A. A. Poot, G. H. M. Engbers, T. Beugeling, W. G. van Aken, J. Feijen and M. J. A. van Luyn, Journal of Biomedical Materials Research, 2001, 55, 368-378.

18. C. R. Yang, Bull. Mat. Sci., 2012, 35, 913-918.

19. H. H. Yoo, M. Lee, M. W. Lee, S. Y. Lim, J. Shin and D. H. Kim, Planta Med., 2007, 73, 444-450.

The foregoing is illustrative of the present invention, and is not to be construed as limiting thereof. The invention is defined by the following claims, with equivalents of the claims to be included therein.

The invention claimed is:

1. A live cell construct, comprising:
  (a) a neutralized collagen hydrogel support comprising:
    i) a first surface;
    ii) a second surface; and
    iii) an intermediate surface between the first surface and second surface and comprising a gradient of cross-linked neutralized collagen hydrogel, wherein the gradient of cross-linked neutralized collagen hydrogel has a higher density near the second surface than near the first surface; and
  (b) a self-renewing monolayer of live primary epithelial cells comprising undifferentiated and/or differentiated live primary epithelial cells formed on the first surface of the cross-linked neutralized collagen hydrogel support, wherein the self-renewing monolayer is maintained or increased for at least 1 day;
  wherein the neutralized collagen hydrogel support is resistant to cell-induced contraction; and wherein the self-renewing monolayer of live primary epithelial cells provides a transepithelial electrical resistance (TEER) of at least 100 Ohms per square centimeter ($\Omega$/cm$^2$).

2. The construct of claim 1, wherein the gradient of cross-linked neutralized collagen comprises a stiffness between about 100 Pa to about 1,000 Pa.

3. The construct of claim 1, wherein the epithelial cells are selected from the group consisting of mammalian, avian, reptilian, amphibian, and insect cells.

4. The construct of claim 1, wherein the epithelial cells are gastrointestinal epithelial cells, urinary epithelial cells, respiratory epithelial cells, reproductive epithelial cells, endocrine and endocrine gland epithelial cells, lymph vessel epithelial cells, blood vessel epithelial cells, or ventricular ependyma epithelial cells.

5. The construct of claim 1, wherein the live undifferentiated epithelial cells are human cells.

6. The construct of claim 1, wherein the epithelial cells are not malignant cells.

7. The construct of claim 1, wherein the epithelial cells are from the colon, small intestine, stomach, esophagus, tongue, nasopharynx, oropharynx, laryngeopharynx, pancreas, kidney, ladder, trachea, lungs, testes, ovaries, ducts of the reproductive tract, endometrium, thyroid gland, adrenal gland, parathyroid gland, ventricular ependyma, brain or combinations thereof.

8. The construct of claim 1, further comprising: a culture medium contacting said self-renewing monolayer of live primary epithelial cells, which culture medium sustains said monolayer of live cells.

9. The construct of claim 8, wherein said culture medium comprises a short-chain fatty acid.

10. The construct of claim 1, wherein said support is porous.

11. The construct of claim 1, said first surface having a plurality of wells formed therein, each of said wells having a top opening, side walls and a floor;
  said epithelial cell monolayer extending onto said well side walls and floors, with said well top openings remaining uncovered, to form open cell lumens in said wells.

12. The construct of claim 1, wherein the self-renewing monolayer of live primary epithelial cells is a continuous self-renewing monolayer of live primary epithelial cells.

\* \* \* \* \*